United States Patent [19]

Rice et al.

[11] Patent Number: 5,476,784
[45] Date of Patent: Dec. 19, 1995

[54] GONOCOCCAL ANTI-IDIOTYPIC ANTIBODIES AND METHODS AND COMPOSITIONS USING THEM

[76] Inventors: Peter A. Rice, 55 Norfolk Rd., Chestnut Hill, Mass. 02167; Sunita Gulati, 14 Wheeler St., Gloucester, Mass. 01930; Daniel P. McQuillen, 9 Holland Ter., Needham, Mass. 02192

[21] Appl. No.: 43,663

[22] Filed: Apr. 6, 1993

[51] Int. Cl.$^6$ .............................. C12N 5/12; C12N 15/02; C07K 16/42; C07K 16/18
[52] U.S. Cl. ................... 435/240.27; 530/387.2; 530/388.4; 530/388.2; 530/387.5; 435/240.2; 435/172.2; 435/70.2; 435/7.32
[58] Field of Search .......................... 530/387.2, 387.5, 530/388.4, 388.2; 424/85.8; 435/172.2, 70.21, 7.32, 240.27, 240.2, 70.2

[56] References Cited

U.S. PATENT DOCUMENTS 4,699,880  10/1987  Goldstein ............................ 435/172.2

OTHER PUBLICATIONS

Harris, W. J. et al., TiBTECH, 11:42–44, Feb. 1993.
Stone, B., Science, 259:1243, 26 Feb. 1993.
Fitzer–Schiller, G., The Washington Post, D3, Jan. 19, 1993.
Spaulding, B. J., Bio/Technology, 11:428–429, Apr. 1993.
Waldmann, T. A., Science, 252:1657–1662, 21 Jun. 1991.
Brossay, L. et al., J. Immunology, 151(1):234–243, Jul., 1993.
Kennedy, R. C. et al., BioTechniques, 3(5):404–409, 1985.
Morrison, Sherie L., Science, 229:1202–1207, 1985.
Queen, C. et al, PNAS, 86:10029–10033, Dec. 1989.
Apicella, M. A., M. A. J. Westerink, S. A. Morse, H. Schneider, P. A. Rice and J. M. Griffiss. 1986. Bactericidal antibody response of normal human serum to the lipooligosaccharid Neisseria gonorrhoeae. J. Infect. Dis. 153:520–526.
Apicella, M. A., R. E. Mandrell, M. Shero, M. E. Wilson, J. McLeod Griftis, G. F. Brooks, C. Lamarel, J. F. Breen and P. A. Rice. 1990. Modification of sialic acid of Neisseria gonorrhoeae lipooligosaccharide epitope expression in human urethral exudates: an immunoelectron microscopic analysis. J. Infect. Dis. 162:506–512.
Britigan, B. E., M. S. Cohen and P.F. Sparling. 1985. Gonococcal infection: a model of molecular pathogenesis. N. Eng. J. Med. 312:1683–1694.
Brodin, N. T., J. Dahmén, B. Nilsson, L. Messter, S. Mårtenson, J. Heldrup, H. O. Sjögren and A. Lundblad. 1988. Monoclonal antibodies produced by immunization with neoglycoproteins containing Galα1→4β1→4Glcβ–O and Galα1→4β1→4GlcNAcβ–O residues: useful immunochemical and cytochemical reagents for blood group P antigens and a differentiation marker in Burkitt lymphoma and other B–cell malignancies. Int. J. Cancer. 42:185–194.
Brooks, G. F. and C. J. Lammel. 1989. Humoral immune response to gonococcal infection. Clin. Micro. Rev. 2:S5–S10.
Brossay, L., G. Paradis, A. Pépin, E. Gagnon, L. Coté, J. Hébert. 1992. Poster Presentation II–4, p. 148, The Eighth International Pathogenic Neisseria Conference, Oct. 4–9, 1992 (Cuernavaca, Mexico).
CDC. 1991. Pelvic Inflammatory Disease: Guidelines for Prevention and Management. MMWR 40:1–25.
CDC. 1982. Sexually transmitted diseases treatment guidelines. MMWR 31:37S–42S 375–425.
CDC. 1984. Chromosomally mediated resistant Neisseria gonorrhoeae–United States. MMWR 33:408–410.
Cohen, I. R., D. S. Kellogg and L. C. Norins. 1969. Serum antibody response in experimental human gonorrhoeae: immunoglobulins G, A and M. Br. J. Ven. Dis. 45:325–327.
Densen, P., S. Gulati and P. A. Rice. 1987. Specificity of antibodies against Neisseria gonorrhoeae that stimulate neutrophil chemotaxis. J. Clin. Invest. 80:78–87.
Fohn, M. J., T. A. Mietzner, T. W. Hubbard, S. A. Morse and E. W. Hook III. 1987. Human immunoglobulin G antibody response to the major gonococcal iron–regulated protein. Infect. Immun. 55:3065–3069.
Glynn, A. A. and M. E. Ward. 1970. Nature and heterogeneity of the antigens of Neisseria gonorrhoeae involved in the serum bactericidal reaction. Infect. Immun. 2:162–168.
Gnehm, H. E., S. I. Pelton, S. Gulati and P. A. Rice. 1985. Characterization of antigens from nontypable Haemophilus influenzas recognized by human bactericidal antibodies. J. Clin. Invest. 75:1645–1658.
Griffiss, H. M., J. P. O'Brien, R. Yamasaki, G. D. Williams, P. A. Rice and H. Schneider. 1987. Physical heterogeneity of Neisserial lipooligosaccharides reflects oligosaccharides that differ in apparent molecular weight, chemical composition, and antigenic expression. Infect. Immun. 55:1792–1800.
Jerne, N. I. 1974. Towards a network theory of the immune system. Ann. Immun. Inst. Pasteur. 125C:373–389.
Joiner, K. A., R. Scales, J. A. Warren, M. M. Frank and P. A. Rice. 1985. Mechanism of action of blocking immunoglobulin G for Neisseria gonorrhoeae. Clin. Invest. 76:1765–1772.
Kasper, D. L., P. A. Rice and W. M. McCormack. 1977. Bactericidal antibody in genital infection due to Neisseria gonorrhoeae. J. Infect. Dis. 135:243–251.
Kennedy, R. C., K. Adler–Storthe, R. D. Henkel, Y. Sanchez, J. L. Melnick and G. R. Dreesman. 1983. Immune response to hepatitis B surface antigen: enhancement by prior injection of antibodies to the idiotype. Science 221:853–855.
Kennedy, R. C., J. W. Eichberg, R. E. Landford and G. R. Dressman. 1986. Anti–idiotypic vaccine for type B viral hepatitis in chimpanzees. Science 232:220–223.

(List continued on next page.)

Primary Examiner—Margaret Parr
Assistant Examiner—Susan A. Loring
Attorney, Agent, or Firm—Fish & Neave; Margaret A. Pierri; Immac J. Thampoe

[57] ABSTRACT

The present invention relates to anti-idiotypic antibodies directed against Neisseria gonorrhoeae. This invention also relates to methods and compositions using such anti-idiotypic antibodies for the prophylaxis, treatment and diagnosis of gonorrheal infections.

6 Claims, 12 Drawing Sheets

OTHER PUBLICATIONS

Kieber–Emmons, T., R. E. Ward, S. Raychaudhuri, R. Rein and H. Kohler. 1986. Rational design and application of idiotope vaccines. *Int. Rev. Immunol.* 1:1–26.

Kim, J. J., R. E. Mandrell, H. Zhen, M. A. J. Westerink, J. T. Poolman and J. M. Griffiss. 1988. Electromorphic characterization and description of conserved epitopes of the lipooligosaccharides of group A *Neisseria meningitidis*. *Infect. Immun.* 56:2631–2638.

Lambden, P. R., J. E. Heckels, H. McBride and P. J. Watt. 1981. The identification and isolation of novel pilus types produced by variants of *Neisseria gonorrhoeae* P9 following selection in vivo. *FEMS. Microbiol. Lett.* 10:339–341.

Lammel, C. J., R. L. Sweet, P. A. Rice, J. S. Knapp, G. K. Schoolnik, D. C. Heilbron and G. F. Brooks. 1985. Antibody–antigen specificity in the immune response to infection with *Neisseria gonorrhoeae*. *J. Infect. Dis.* 152:990–1001.

Mandrell, R. E., H. Schneider, M. A. Apicella, W. D. Zollinger, P. A. Rice and J. M. Griffiss. 1986. Antigenic and physical diversity of *Neisseria gonorrhoeae* lipooligosaccharides. *Infect. Immun.* 54:63–69.

Mandrell R. E., J. M. Griffiss and B. E. Macher. 1988. Lipooigosaccharides (LOS) of *Neisseria gonorrhoeae* and *Neisseria meningitidis* have components that are immunochemically similar to precursors of human blood group antigens: carbohydrate sequence specificity of the mouse monoclonal antibodies that recognize crossreacting antigens on LOS and human erythrocytes. *J. Exp. Med.* 168:107–126.

Mandrell, R. E. 1992. Further antigenic similarities of *Neisseria gonorrhoeae* lipooligosaccharides and human glycosphingolipids. *Infect. Immun.* 60:3017–3020.

Morse, S. A., S. Stein and J. Hines. 1974. Glucose metabolism in *Neisseria gonorrhoeae*. *J. Bact.* 120:702–714.

Newhall, W. J., W. D. Sawyer, and R. A. Haak. Cross–linking analysis of the outer membrance proteins of *Neisseria gonorrhoeae*. *Infect. Innum.* 28:785–791.

Nisonoff, A. and E. Lamoyi. 1981. Implications of the presence of an internal image of the antigen in anti–idiotypic antibodies: possible application to vaccine production. *Clin. Immunol. Immunopathol.* 21:397–406.

Rice, P. A. and D. L. Kasper. 1977. Characterization of gonococcal antigens responsible for induction of bactericidal antibody in disseminated infection. *J. Clin. Invest.* 60:1149–1158.

Rice, P. A. and D. L. Kasper. 1982. Characterization of serum resistance of *Neisseria gonorrhoeae* that disseminate. *J. Clin. Invest.* 70:157–167.

Rice. P. A., H. E. Vayo, M. R. Tam and M. S. Blake. 1986. Immunoglobulin G antibodies directed against protein III block killing of serum resistant *Neisseria gonorrhoeae* by immune serum. *J. Exp. Med.* 164:1735–1748.

Rice, P. A. 1989. Molecular basis for serum resistance in *Neisseria gonorrhoeae*. *Clin. Micro. Rev.* 2S:S112–S117.

Roberts, R. B. 1967. The interaction in vitro between Group B meningococci and rabbit polymorphonuclear leukocytes. *J. Exp. Med.* 126:795–817.

Ross, S. C. and P. Densen. 1985. Opsonophagocytosis of *Neisseria gonorrhoeae*: interaction of local and disseminated isolates with complement and neutrophils. *J. Infect. Dis.* 151:33–41.

Schoolnik, G. K. and Mietzner, T. A. 1992. Vaccines against gonococcal infections. In: G. C. Woodrow and M. M. Levine (ed.), *New Generation Vaccines*, Marcel Dekker, Inc. New York, 565–597.

Schoolnik, G. K. and Z. A. McGee. 1985. Gonococcal vaccine development strategies: summary of the recommendations of a National Institutes of Health vaccine panel. In: G. K. Schoolnik, G. F. Brooks, S. Falkow, C. E. Frasch, J. S. Knapp, J. A. McCutchan and S. A. Morse (ed.), *The pathogenic neisseria*, ASM, Washington D.C., 329–331.

Schreiber, J. R., M. Patarawan, M. Tosi, J. Lennon and G. B. Pier. 1990. Anti–idiotype–induced lipo–oligosaccharide specific antibody response to *Pseudomanas aeroginosa*. *J. Immun.* 144:1023–1029.

Schreiber, J. R., G. B. Pier, M. Grout, K. Nixon and M. Patawaran. 1991. Induction of opsonic antibodies to *Pseudomonas aeroginosa* mucoid exopolysaccharide by an anti–idiotypic monoclonal antibody. *J. Infect. Dis.* 164:507–514.

Stein, K. E. and T. Soderstrom. 1984. Neonatal administration of idiotype or anti–idiotype primes for protection against *Escherichia coli* K13 infection in mice. *J. Exp. Med.* 160:1001–1011.

Swanson, J. 1979. Studies on gonococcus infection XVIII. $^{125}$I–labeled peptide mapping of the major protein of the gonococcal cell wall outer membrane. *Infect.Immun.* 23:799–810.

Swanson, J. 1982. Colony opacity and protein II compositions of gonococci. *Infect.Immun.* 37:359–368.

Tramont, E. C., J. C. Sadoff and M. S. Artenstein. 1974. Cross–reactivity of *Neisseria gonorrhoeae* and *Neisseria meningitidis* and the nature of antigens involved in the bactericidal reaction. *J. Infect. Dis.* 130:240–247.

Tramont, E. C. and J. Ciak. 1978. Antigonococcal antibodies in genital secretions. In: G. F. Brooks, E. C. Gotschlich, W. D. Sawyer and F. E. Young (ed.), *Immunobiology of Neisseria gonorrhoeae* (ASM, Washington D.C.), 274–278.

Tramont, E. C., J. W. Boslego, R. Chung, D. McChesney, J. Ciak, J. Sadoff, M. Piziak, C. C. Brinton, S. Wood and J. Bryan. 1985. Parenteral gonococcal pilus vaccine. In: G. K. Schoolnik, G. F. Brooks, S. Falkow, C. E. Frasch, J. S. Knapp, J. A. McCutchan and S. A. Morse. (eds.), *The pathogenic neisseria*. (ASM, Washington D.C.), 316–322.

Tramont, E. C. 1989. Gonococcal vaccines. *Clin. Micro. Rev.* 2S:S74–S77.

Ward, M. E., P. J. Watt and J. N. Robertson. 1974. The human fallopian tube: a laboratory model for gonococcal infection. *J. Infect. Dis.* 129:650–659.

Ward, M. E., P. R. Lambden, J. E. Heckels and P. J. Ward. 1978. The surface properties of *Neisseria gonorrhoeae*: determinants of susceptibility to antibody complement killing. *J. Gen. Micro.* 108:205–212.

Ward, M. E., P. R. Lambden, J. E. Heckels and P. J. Ward. 1978. The surface properties of *Neisseria gonorrhoeae*: determinants of susceptibility to antibody complement killing. *J. Gen. Micro.* 108:205–212.

Ward, M. M., R. E. Ward, J. H. Huang and H. Kohler. 1987. Idiotope vaccine against *Streptococcus pneumonia*: A precursor study. *J. Immunol.* 139:2775–2780.

Washington, A. E. 1982. Update on treatment recommendations for gonococcal infections. *Rev. Infect. Dis.* 4S:S758–S771.

Westerink, M. A. J., A. A. Campagnari, M. A. Wirth and M. A. Apicella. 1988. Development and characterization of an anti–idiotype antibody to the capsular polysaccharide of *Neisseria meningitidis* serogroup C. *Infect. Immun.* 56–1120–1127.

—○— NO COMPLEMENT
—◆— TOTAL COMPLEMENT
—△— C5-DEFICIENT COMPLEMENT
—□— HI TOTAL COMPLEMENT
--◇-- HI C5-DEFICIENT COMPLEMENT

—○— NO COMPLEMENT
—◆— TOTAL COMPLEMENT
—△— C5-DEFICIENT COMPLEMENT
—□— HI TOTAL COMPLEMENT
—◇— HI C5-DEFICIENT COMPLEMENT

GONOCOCCAL ANTI-IDIOTYPIC ANTIBODIES AND METHODS AND COMPOSITIONS USING THEM

TECHNICAL FIELD OF THE INVENTION

The present invention relates to anti-idiotypic antibodies directed against Neisseria gonorrhoeae. This invention also relates to methods and compositions using such anti-idiotypic antibodies for the prophylaxis, treatment and diagnosis of gonorrheal infections.

BACKGROUND OF THE INVENTION

The sexually transmitted disease, gonorrhea, poses a worldwide risk as one of the most commonly reported communicable diseases. Gonorrhea is caused by the bacterium Neisseria gonorrhoeae, a gram negative diplococcus. Although the pathogen primarily infects mucous membranes, it is capable of invading tissues and evading host defenses. N. gonorrhoeae is the causative agent of a spectrum of sequelae. These range from asymptomatic mucosal infection to significant disease syndromes in both men and women. The more serious of such syndromes include, for example, disseminated gonococcal infection (DGI) in men and women, as well as salpingitis or pelvic inflammatory disease (PID) in women. Either salpingitis or PID may themselves lead to long-term sequelae, including ectopic pregnancy and infertility. Other important sequelae, sometimes requiring surgical intervention, include recurrent infection, chronic pelvic pain, dyspareunia, pelvic adhesions and other inflammatory residua.

It has been estimated that in the United States, the direct and indirect costs of treating PID and associated ectopic pregnancy and infertility were 2.6 billion dollars in 1984 (65). The total direct costs were estimated to be 2.18 billion dollars in 1990, with indirect costs of 1.54 billion dollars. Assuming constant inflation and incidence rates of PID, the total cost of this disease is projected to reach 8 billion dollars by the year 2000 (6).

Despite public health efforts to control gonococcal infections and the availability of effective antibiotic therapies in the United States, there are approximately one million cases of gonorrhea reported annually to the Centers for Disease Control (CDC) (9). A substantial proportion of all cases of gonorrhea occur in asymptomatically infected individuals who are the source of most new cases within a community (4). The increasing prevalence of antibiotic-resistant strains has complicated treatment of the infection. (7, 8, 64).

N. gonorrhoeae has multiple virulence factors. The surface components of this pathogen play an important role in attaching to and invading host cells, while providing potential targets for the host immune response. Gonococcal infections elicit local and systemic humoral and cellular immune responses to several components which are exhibited as surface exposed antigens of the bacterium, particularly pili, porin (Por) or protein I (PI), opacity associated proteins (Opas) or protein IIs, Rmp or protein III, and lipooligosaccharides (LOSs) (5). Pili, Opa, Por and LOS are all implicated in attachment to and invasion of the host and all display considerable variation on their surface exposed regions (33, 56, 57). The intra- and inter-strain variations of gonococcal surface components have led to hypotheses regarding tissue specificity at different sites and the organism's potential for reinfection and continued virulence.

In both symptomatic and asymptomatic patients, gonococcal infections have been shown to stimulate increased levels of anti-gonococcal serum immunoglobulins. The peripheral humoral response is predominately IgG (mostly subclass IgG3), with lesser amounts of IgM and IgA (11). Quantitatively, the antibody response is primarily directed against the pili, Opa proteins and LOS. Local antibodies are present in genital secretions, but in reduced amounts (59), and may be directed against different antigenic targets than those in serum (34). The predominant class of antibodies present in secretions is also IgG (mostly IgG3) and not secretory IgA (sIgA) (5). Antibodies against LOS are present as well, but in lesser amounts than those against pili, Por and Opa. Although patients infected with N. gonorrhoeae may show an antibody response to many gonococcal antigens, N. gonorrhoeae isolated from patients with disseminated infection (DGI) are resistant to the bactericidal action of normal human serum (NHS) and of most convalescent sera (46). This serum-resistant phenotype, termed stable serum resistance (SR), may enable the organism to evade local defenses, penetrate mucosal barriers and disseminate via the bloodstream.

Upon subculture, many strains of gonococci become phenotypically sensitive to killing by NHS or serum sensitive (46). These organisms are termed serum sensitive (SS) (or unstably serum-resistant [SR]). Such organisms are frequently isolated from women with severe manifestations of local inflammation or clinically evident PID. Acute salpingitis, the pathologic counterpart of PID (caused by SS gonococci), rarely progresses to bacteremic illness or DGI. This suggests that the intense local inflammatory response, generated by SS gonococci, may serve to contain the infection and prevent bacteremia, although at the cost of damaging the local tissues. SS gonococci generate significantly greater amounts of the complement derived chemotactic peptide, C5a, than do SR gonococci (12). This may be responsible for the polymorphonuclear leukocyte (PMN) mediated inflammatory response that is produced by SS gonococci.

The development of antibiotic-resistant strains of N. gonorrhoeae, has rendered control of this infection increasingly difficult. The potential to undertreat gonococcal infection has accelerated the need for an anti-gonococcal vaccine. The prevention of gonococcal infection, particularly the severe complications of PID, has been the goal of many investigators. Ongoing attempts to develop an effective anti-gonococcal vaccine, however, have been plagued with several difficulties.

Attempts to use individual surface components of the pathogen as targets for conventional vaccines have been unsuccessful because of their antigenic variability. Pilus vaccines have been protective only against infection with the homologous strain (used to make the pilus vaccine) and Por vaccination has been unsuccessful even in human experimental challenge. In addition, N. gonorrhoeae express marked phenotypic heterogeneity, typically shifting from one antigenic form to another at a frequency of >1 in $10^3$ organisms (60, 61) making the surface of this organism a moving target for most vaccine strategies. Although the vaccine candidates have provoked antibody responses, the antibodies and immune responses produced have not been broadly protective.

LOS is an important virulence determinant of N. gonorrhoeae. Considerable evidence supports the role of LOS as a major target of bactericidal antibody directed to the surface of N. gonorrhoeae (1, 12, 17, 43, 58). Antibodies to LOS have several important functions: bactericidal activity, complement activation through the classical or alternative complement pathways (1), and opsonic activity (12). Additionally, LOS has been shown to be the most effective gonococcal antigen to induce a functional antibody response to homologous and heterologous gonococci (63).

The monoclonal antibody (mAb) 2C7 (36), detects a LOS derived oligosaccharide (OS) epitope that appears to be widely conserved and expressed amongst clinical isolates of gonococci. Typically, saccharides are T-cell independent antigens. When administered alone as immunogens, they generally elicit only a primary antibody response. In addition, oligosaccharides are small (<10 saccharide units) (20), and would likely require additional biochemical derivitization to render them immunogenic. The use of such oligosaccharides as vaccine candidates, therefore, is limited in several respects.

Internal image determinants have been proposed for use in vaccines (42). By means of mAb technology, a protective antibody (Ab1) to an epitope of interest on the pathogen can be produced. The particular antibody (Ab1) can be purified and subsequently used as an immunogen to elicit an anti-idiotypic antibody (Ab2) which may be an internal image of the original epitope on the pathogen.

As predicted by the Jerne "network" theory (24), immunization with an anti-idiotypic antibody (Ab2) that is directed against antigen combining sites of primary antibody (Ab1), may elicit a humoral immune response specific for the nominal antigen. The resulting anti-anti-idiotypic antibody (or Ab3) should react with the original primary antigen. If the primary antigen is an oligosaccharide (and therefore expected to give a T-cell independent immune response), then immunization with Ab2 (the protein equivalent) may elicit a T-cell dependent response.

Anti-idiotype antibodies have been employed to successfully raise protective antibodies against various pathogens in animal systems (28, 29, 40, 51 52, 53, 66). An anti-idiotypic antibody will not contain the nominal antigen (as is the case with saccharide antigens), thus avoiding any undesirable adverse effects associated with use of that antigen as an immunogen. Anti-idiotypic antibodies are protein antigens that often (but not always) act as a T-cell dependent immunogen (30).

The need exists for an agent useful for the prevention or treatment of gonorrhea targeted to the prevention of gonococcal salpingitis, an infection that may be associated with debilitating and chronic pelvic pain, infertility and ectopic pregnancy (50). Another important objective is to prevent transmission of the organism from an infected but asymptomatic host to an otherwise immune sexual consort. This is important because a substantial fraction of all cases of gonorrhea in both men and women are asymptomatic, and asymptomatically infected, sexually active persons are probably the major source of most new infections. Accordingly, a gonococcal vaccine that only attenuates the severity of symptomatic gonorrhea could result in a higher ratio of asymptomatic/symptomatic cases and as a result, such a vaccine might promote the spread of gonorrhea, unless it also prevents transmission (49).

SUMMARY OF THE INVENTION

The present invention generally solves the problems referred to above by providing anti-idiotypic antibodies and fragments thereof, the antigen binding sites of which immunospecifically bind to antibodies that recognize oligosaccharide epitopes of N. gonorrhoeae which are not present in human blood group antigens. Also provided are cells which produce the anti-idiotypic antibodies and fragments thereof according to this invention and processes for producing such antibodies and fragments by culturing those cells.

The anti-idiotypic antibodies and fragments thereof, according to this invention, are useful in methods and compositions for the prophylaxis, treatment and detection of N. gonorrhoeae infections.

panel A—24-1 opsonized with mAb 2C7; panel B—24-1 nonopsonized; panel C—WG opsonized with mAb 2C7; panel D—WG nonopsonized; panel E—71H opsonized with mAb 2C7; panel F—71H nonopsonized. Complement sources are as indicated.

FIGS. 13A–13F, together, depict the increase in ingestion of organisms by PMNs after opsonization with mAb 2C7 (Ab1), as reflected by decreased binding of SAPETR and corresponding decrease in red fluorescence. The results are indicated as follows: FIG. 13A—24-1 opsonized; FIG.

Figure 13A:
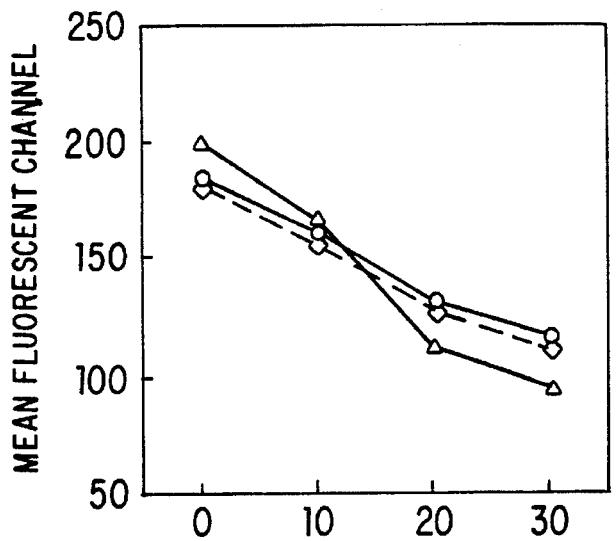
Figure 13B:
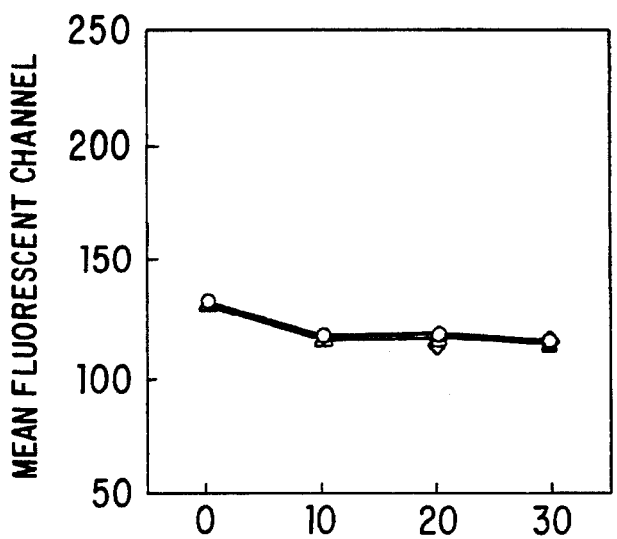
Figure 13C:
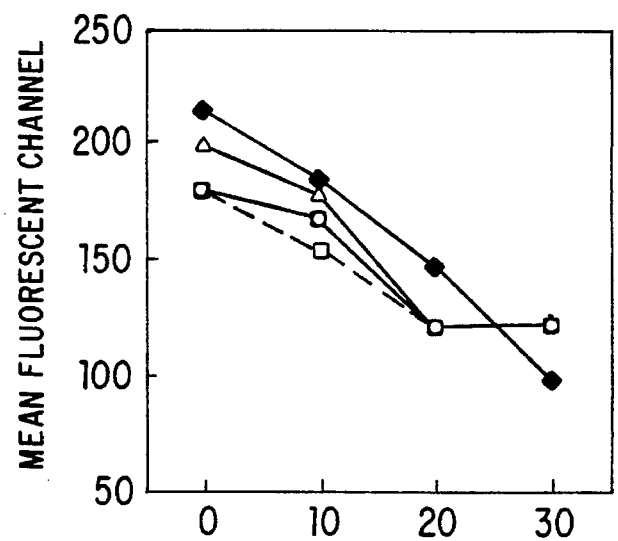
Figure 13D:
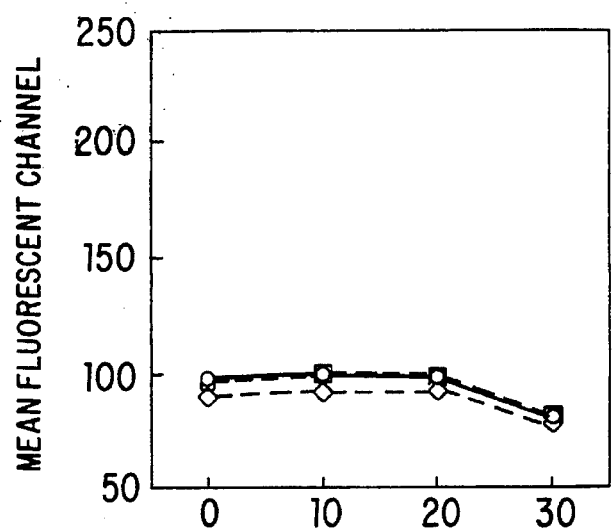
Figure 13E:
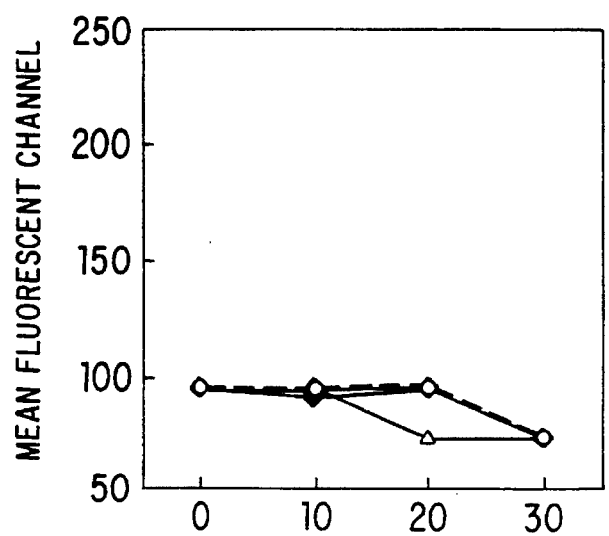
Figure 13F:
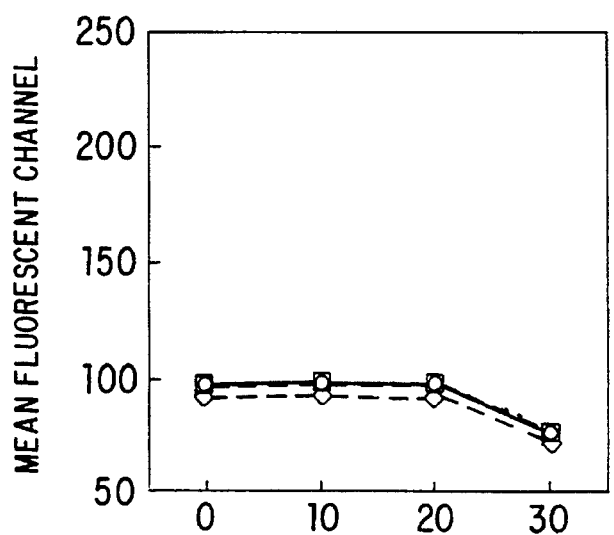

13B—24-1 nonopsonized; FIG. 13C—WG opsonized; FIG. 13D—WG nonopsonized; FIG. 13E—71H opsonized; FIG. 13F—71H nonopsonized. The X-axis represents time (minutes) of incubation at 37° C. with PMNs. Complement sources present are as indicated.

Figure 14:
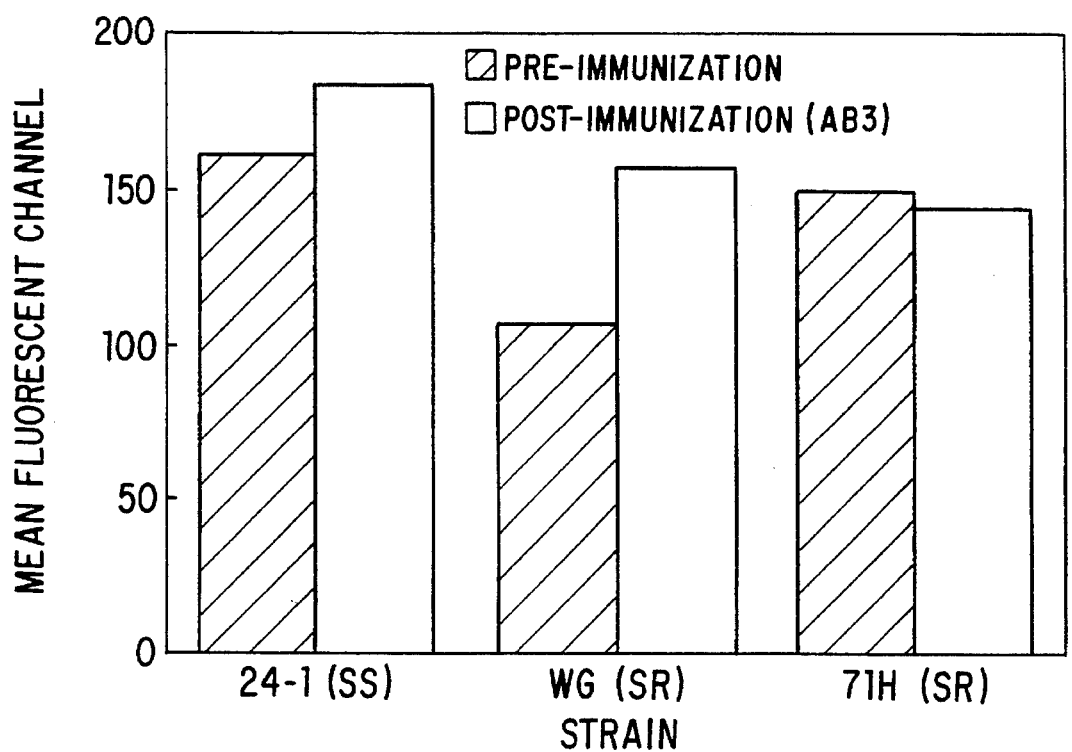

FIG. 14 depicts the effect of opsonizing antibody Ab3, produced by immunizing xenogeneic rabbits with Ab2 (CA1), on the adherence of serum sensitive (SS) and serum resistant (SR) gonococcal strains to PMNs.

Figure 15C:
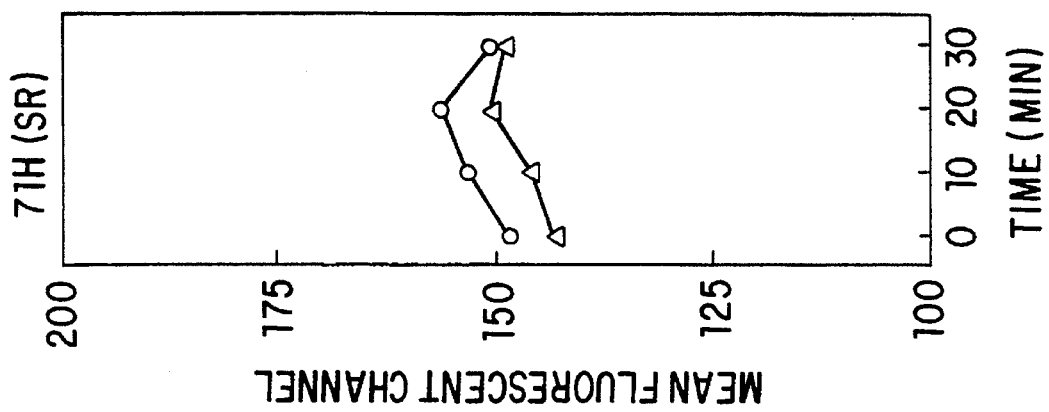
Figure 15B:
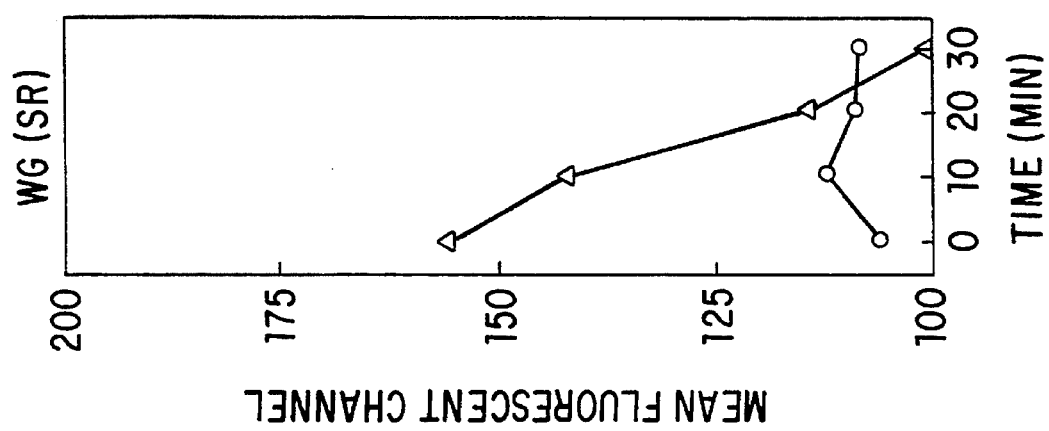
Figure 15A:
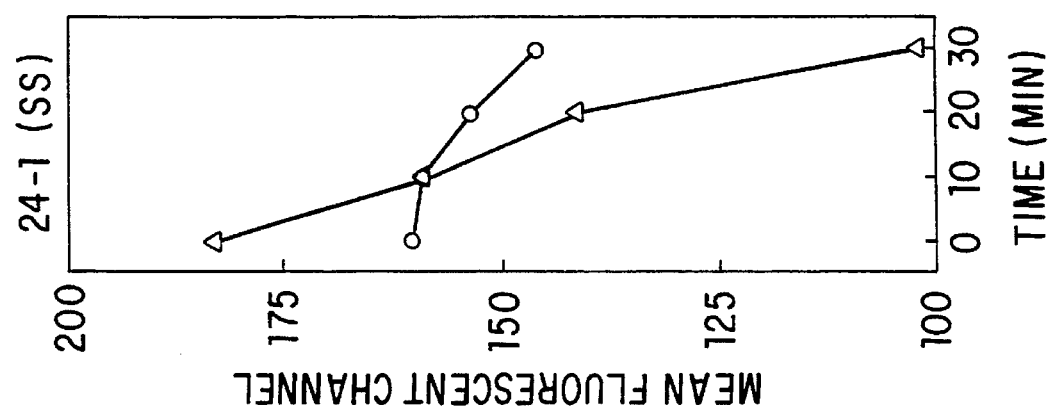

FIGS. 15A–15C, together, depict the increase in ingestion of serum sensitive (SS—FIG. 15A) and serum resistant (SR—FIGS. 15B and 15C) gonococcal strains by PMNs after opsonization with antibody Ab3 (produced in xenogeneic rabbits), reflected by decreased binding of SAPETR and corresponding decrease in red fluorescence. Organisms were opsonized with either pre- (0—0) or post-mAb CA1 (Ab2) immunization (Δ—Δ) rabbit sera.

DETAILED DESCRIPTION OF THE INVENTION

Definitions

As used herein, an "antibody" is an intact immunoglobulin molecule comprising two each of immunoglobulin light and heavy chains. Accordingly, antibodies include intact immunoglobulins of types IgA, IgG, IgE, IgD, IgM (as well as subtypes thereof), wherein the light chains of the immunoglobulin may be of types kappa or lambda.

As used herein, antibody "fragments" are portions of intact immunoglobulins that retain antigen binding specificity, for example, Fab fragments, Fab' fragments, F(ab')$_2$ fragments, F(v) fragments, fragments comprised of one or more complementarity determining region(s) (CDR), heavy chain monomers or dimers, light chain monomers or dimers, dimers consisting of one heavy and one light chain, and the like.

As used herein, "monoclonal antibodies" are monospecific antibodies produced initially by a single clone of antibody forming cells.

As used herein, a "recombinant antibody" is an antibody produced by or cell transformed with DNA encoding the light and heavy chains of a given immunoglobulin molecule.

As used herein, a "humanized recombinant antibody" is an antibody initially derived from a nonhuman mammal in which recombinant DNA technology has been used to substitute some or all of the amino acids not required for antigen binding with amino acids from corresponding regions of a human immunoglobulin light or heavy chain.

As used herein, a "chimeric recombinant antibody" is an antibody derived initially from a nonhuman mammal, in which recombinant DNA technology has been used to replace all or part of the hinge and constant regions of the heavy chain and/or the constant region of the light chain, with corresponding regions from a human immunoglobulin light chain or heavy chain.

As used herein, "immunoprophylactically effective" means the ability to induce in a normal individual an immune response sufficient to protect said patient for some period of time against N. gonorrhoeae infection.

As used herein, "immunotherapeutically effective" means the ability to induce in a treated patient an immune response sufficient to prevent some or all of the effects of N. gonorrhoeae infection.

As used herein, "diagnostically effective" means the ability to detect antibodies against the oligosaccharide antigens of N. gonorrhoeae in vivo or in vitro.

Anti-Idiotypic Antibodies And Their Use In Compositions And Methods According To This Invention One aspect of the present invention is directed to anti-idiotypic antibodies or fragments thereof, that react with an idiotype directed against an oligosaccharide antigen of N. gonorrhoeae, which oligosaccharide epitope is not present in human blood group antigens, and to cells which produce said antibodies or fragments.

The technology for producing monoclonal antibodies is known to those of skill in the art. Briefly, an immortal cell line (typically murine myeloma cells) is fused to lymphocytes (typically splenocytes) from a mammal immunized with a preparation comprising a given antigen, and the culture supernatants of the resulting hybridoma cells are screened for antibodies against the antigen (31).

To produce the anti-idiotypic monoclonal antibodies of the present invention, one may use any antibody (Ab1) reactive with an oligosaccharide antigen of N. gonorrhoeae as the immunogen, or hybridoma cells producing said antibody. We used mAb 2C7 producing hybridoma cells as the immunogen (Ab1) to produce the anti-idiotypic monoclonal antibody (Ab2) exemplified in this invention. We prepared mAb 2C7 producing hybridoma cells by using spleen cells from mice immunized with outer membranes from N. gonorrhoeae. Alternatively, one may also use purified LOS of N. gonorrhoeae as the immunogen to produce Ab1.

Another approach for the production of Ab1, would be to use the exemplified anti-idiotypic antibody of this invention as the immunogen to produce anti-anti-idiotypic antibodies (Ab3) which are functionally similar to mAb 2C7. These Ab3 antibodies may then be used to generate antibodies that react with an idiotype directed against an oligosaccharide antigen of N. gonorrhoeae but not directed against human blood group antigens.

Immunization may be accomplished using standard procedures. The unit dose and immunization regimen depend on the species of mammal immunized, its immune status and factors including the body weight of the mammal. Typically, the immunized mammals are bled and the serum from each blood sample is assayed for particular antibodies using appropriate screening assays.

Typically, the immortal cell line (e.g., a myeloma cell line) is derived from the same mammalian species as the lymphocytes. Preferred immortal cell lines are mouse myeloma cell lines that are sensitive to culture medium containing hypoxanthine, aminopterin and thymidine ("HAT medium"). HAT-sensitive mouse myeloma cells are fused to mouse splenocytes using polyethylene glycol (e.g., PEG 3350) (35). Hybridoma cells resulting from the fusion are then selected using HAT medium, which kills unfused and unproductively fused myeloma cells (unfused splenocytes die after several days because they are not transformed). Hybridomas producing a desired antibody are detected by screening the hybridoma culture supernatants using assays which detect MAbs having the desired specificity.

To produce anti-idiotypic antibodies according to the present invention, hybridoma cells that test positive in screening assays as described herein are cultured in a nutrient medium under conditions and for a time sufficient to allow the hybridoma cells to secrete the monoclonal antibodies into the culture medium. Tissue culture techniques and culture media suitable for hybridoma cells are well known. The conditioned hybridoma culture supernatant may be collected and the antibodies optionally further purified by conventional methods.

Alternatively, the desired antibody may be produced by injecting the hybridoma cells into the peritoneal cavity of a mouse primed with 2,6,10,14-tetramethylpentadecane (PRISTANE, Sigma Chemical Co., St. Louis, Mo.). The hybridoma cells proliferate in the peritoneal cavity, secreting the antibody which accumulates as ascites fluid. The antibody may be harvested by withdrawing the ascites fluid from the peritoneal cavity with a syringe.

Recombinant antibodies of the present invention may be produced using conventional recombinant DNA techniques, e.g., by transforming a host cell with a suitable expression vector comprising DNA encoding the light and heavy immunoglobulin chains of a desired antibody. In addition, it is possible to produce recombinant chimeric antibodies, wherein some or all of the hinge and constant regions of the heavy chain and/or the constant region of the light chains of an antibody of this invention have been substituted with corresponding regions of an immunoglobulin light or heavy chain of a different species, and recombinant "humanized" antibodies prepared by CDR grafting, in which all but the complementarity determining region(s) of an antibody are replaced by corresponding parts of a human antibody, to reduce the antigenicity of the antibody (26, 62, 68).

Furthermore, the present invention includes antigen binding fragments of the antibodies described herein, such as Fab, Fab', F(ab)$_2$, and F(v) fragments, fragments comprised of one or more complementarity determining region(s) (CDRs), single chain antibodies, heavy chain monomers or dimers, light chain monomers or dimers, and dimers consisting of one heavy chain and one light chain. Such antibody fragments may be produced by chemical methods, e.g., by cleaving an intact antibody with a protease, such as pepsin or papain, or via recombinant DNA techniques, e.g., by using host cells transformed with truncated heavy and/or light chain genes. Synthetic methods of generating such fragments are also contemplated. Heavy and light chain monomers may similarly be produced by treating an intact antibody with a reducing agent such as dithiothreitol or β-mercaptoethanol or by using host cells transformed with DNA encoding either the desired heavy chain or light chain or both.

In one embodiment of the present invention, anti-idiotypic antibodies or fragments thereof that react with an idiotype that is directed against an oligosaccharide antigen of N. gonorrhoeae may be administered to uninfected individuals to induce a specific immune response directed against gonococcal organisms or cells bearing said oligosaccharide antigen. Such an immune response can be immunoprophylactic in character in that it would prevent an infection should the recipient be exposed to the gonococcal organism.

In another embodiment, patients already infected with N. gonorrhoeae or exhibiting symptoms of gonorrheal infection may be immunotherapeutically treated with the antibodies or fragments produced by using the antibodies (Ab2), (Ab3) or fragments of the present invention as immunogen.

For therapeutic and prophylactic uses, the anti-idiotypic antibodies and antibody fragments of the present invention may be formulated as a pharmaceutical composition comprising an immunotherapeutically or immunoprophylactically effective amount of the antibody or antibody fragment admixed with a pharmaceutically acceptable carrier, the amount being effective to significantly kill the infecting organism in the presence of complement, or to opsonize the infecting organism to permit phagocytic killing by the host PMNs. In monotherapy for treatment or prophylaxis of diseases characterized by N. gonorrhoeae infection, immunotherapeutically or immunoprophylactically effective amounts per unit dose of an intact antibody range from about 0.1 to about 10 mg/kg patient weight, preferably about 1 mg/kg patient weight. Unit doses should be administered from twice each day to once each day for one week. It will be recognized, however, that lower or higher dosages and other administration schedules may be employed.

The preferred pharmaceutical compositions of this invention are similar to those used for passive immunization of humans with other antibodies. Typically, the antibodies of the present invention will be suspended in a sterile saline solution for therapeutic uses. The pharmaceutical compositions may alternatively be formulated to control release of the active ingredients or to prolong their presence in a patient's system. Numerous suitable drug delivery systems are known and include, e.g., implantable drug release systems, hydrogels, hydroxymethylcellulose, microcapsules, liposomes, microemulsions, microspheres, and the like.

The pharmaceutical compositions of this invention may be administered by any suitable means such as orally, intranasally, subcutaneously, intramuscularly, intravenously, intra-arterially, or parenterally. Ordinarily, intravenous (i.v.) or parenteral administration will be preferred.

It will be apparent to those of ordinary skill in the art that the immunotherapeutically effective or immunoprophylactically effective amount of antibody or fragments thereof of this invention will depend, inter alia, upon the administration schedule, the unit dose of antibody or fragment administered, whether the antibody or fragment is administered in combination with other therapeutic agents, the immune status and health of the patient, the therapeutic activity of the antibody or antibody fragment administered and the judgment of the treating physician.

The anti-idiotypic antibodies or fragments thereof according to the present invention may also be labeled and used in screening methods, diagnostic methods or assays for detecting antibodies reactive with oligosaccharide antigens of N. gonorrhoeae in vitro or in vivo. These include, for example, enzyme-linked immunosorbent assays (ELISAs). For example, samples may be screened for the presence of antibodies reactive with oligosaccharide antigens of N. gonorrhoeae by contacting the sample with a labeled anti-idiotypic antibody of the present invention and detecting the label. Similarly, anti-anti-idiotypic antibodies (Ab3) may also be prepared and used for detecting the presence of gonococcal oligosaccharide (OS) antigen present in clinical samples. Accordingly, this invention includes diagnostic kits comprising detectably labeled anti-idiotypic antibodies or fragments or anti-anti-idiotypic antibodies or fragments of this invention, as a reagent, and complete instructions for using the reagent to detect antibodies reactive with oligosaccharide antigens of N. gonorrhoeae or the oligosaccharide antigens themselves. Detection methods according to this invention may comprise the steps of applying anti-immunoglobulin antibodies to a solid support; applying a biological sample to the solid support; removing the excess biological sample from the solid support; applying detectably labelled antibodies or fragments according to this invention to the solid support; washing the solid support and assaying for the presence of label on the solid support.

Suitable labels may be radioactive, enzymatic, fluorescent, magnetic or chemiluminescent. Radiolabeled antibodies are prepared in known ways by coupling a radioactive isotope such as $^3$H, $^{32}$p, $^{35}$S, $^{59}$Fe $^{125}$I, which can then be detected by gamma counter, scintillation counter or by autoradiography. Anti-idiotypic antibodies and anti-anti-idiotypic antibodies of this invention may be suitably labeled with enzymes such as yeast alcohol dehydrogenase, horseradish peroxidase, alkaline phosphatase, and the like, then developed and detected spectrophotometrically or visually. Suitable fluorescent labels include fluorescein isothiocyanate, fluorescamine, rhodamine, and the like. Suitable chemiluminescent labels include luminol, imidazole, oxalate ester, luciferin, and the like.

In order that this invention may be better understood, the following examples are set forth. These examples are for purposes of illustration only, and are not to be construed as limiting the scope of the invention in any manner.

EXAMPLES

Materials and Methods

I. Strains

Two serum resistant gonococcal strains, WG (DGI-1) (25, 44, 45) and 71H (DGI-5) (12, 43), and one serum sensitive strain 24-1 (12, 36) were used. All strains were stored at −70° C. in 20% glycerol/Tryptic Soy Broth.

II. Antigens (a) Preparation of lipooligosaccharide (LOS)

LOS (containing the 2C7 epitope) was prepared from our prototype serum sensitive strain (SS) of N. gonorrhoeae, 24-1, by a modification of the hot phenol water extraction procedure (18, 67). Organisms were removed from purified frozen culture stocks (−70° C.) and inoculated onto chocolate agar plates. Plates were incubated for 16–18 hours at 37° C. in a candle extinction jar. Overnight growth from one plate was subcultured onto 10 plates (and incubated as above) and then to 100 plates to produce confluent lawns of organisms. The organisms were carefully removed with a sterile rubber spatula (without scraping the agar) and resuspended in 100 ml of ice-cold sterile normal saline (0.9% NaCl). Organisms were centrifuged (5000×g) for 10 minutes, at 4° C., and the pellets washed two times by resuspending the cells in ice-cold normal saline and re-centrifuged. The final pellets were resuspended in 10 ml of sterile cold deionized and distilled water and lyophilized.

Dried whole organisms were resuspended in deionized and distilled water at a ratio of 1 gm/21 ml (wt./vol.), and heated to 65° C., while stirring constantly. Equal volumes of 90% Phenol (Fisher Scientific, Medford, Mass.) were then added and the mixtures stirred constantly at 65° C. for 15 minutes. The mixtures were transferred to 50 ml glass centrifuge tubes, cooled to 10° C. then centrifuged (5000×g) for 15 minutes at 4° C. The top aqueous layers (containing LOS and nucleic acids) were gently removed to a separate tube using Pasteur pipettes without disturbing the intermediate white cloudy layers. Equal volumes of deionized and distilled water were added to residual material in the tubes and the extraction procedures repeated. Aqueous layers were combined and centrifuged to remove insoluble material. The supernatants were then dialyzed (using a 10,000 MW cutoff dialyzing bag; Fisher, Medford, Mass.) in cold distilled deionized water for 2 weeks (changing the water outside thrice weekly). Following dialysis, the LOS was precipitated by adding 6 volumes of cold 0.05M sodium acetate in 95% ethanol at −20° C. for ≧4 hours. Precipitates were removed by centrifugation (5000×g) for 15 minutes at 4° C. and the remaining ethanol was allowed to evaporate. The dried pellets were resuspended in deionized and distilled water and ultracentrifuged (105,000×g) for 3 hours at 4° C. The resulting pellets were washed by resuspending them in distilled and deionized water and ultracentrifuged (as above) repeatedly to remove the remaining nucleic acids (i.e., until the OD measurements [at 280 and 260 nm] of the supernatants were <0.01). The final clear pellets, containing LOS, were resuspended in a small volume (approximately 0.5 ml) of deionized and distilled water and lyophilized. Dried LOS powder was weighed and stored at room temperature. This material was utilized as target antigen in ELISA assays (to screen hybridoma cells for specific antibody production) and as a control immunogen in the animal studies.

(b) Characterization of LOS (i) SDS-PAGE

The purity of the LOS antigen was assessed by sodium-dodecyl-sulfate polyacrylamide gel electrophoresis (SDS-PAGE). Discontinuous Tris-glycine SDS-PAGEs, containing urea, were prepared according to Laemmli's procedure (32). The 14% T separating gels (29.2:0.8 ratio of acrylamide: N,N'-methylene bisacrylamide in 0.375M Tris, 0.1% SDS, pH 8.8; 25% urea) were poured into vertical glass molds and allowed to polymerize at room temperature. The 4% T stacking gels (29.2:0.8 ratio of acrylamide: N,N'-methylene bisacrylamide in 0.125M Tris, 0.1% SDS, pH 6.8; 25% urea) were layered on top of separating gels. Combs (containing 10 mm wide teeth) were inserted into the stacking gels to provide lanes into which the samples were to be added and polymerization of the gels allowed to occur at room temperature. Combs were removed and the lanes were washed with deionized and distilled water.

Prior to electrophoresis, LOS was added to digestion buffer (4.4% SDS in 0.18M Tris-HCl, 14.7% glycerol, 1.4% dithiothritol, pH 6.8; 25% bromophenol blue [1 μg/μl]) and boiled for 10 minutes. To estimate the molecular weights (MW) of each of the electrophoresed LOS samples, molecular weight protein standards (MW 14.4 KD200 KD) from Bio-Rad (Richmond, Calif.) were also prepared in the digestion buffer at a concentration of 5 μl of standard/100 μl of digestion buffer.

Aliquots of 10 μg/10 μl of each sample solution or 10 μl of MW standard solution was added to lanes of the SDS-PAGE and electrophoresed in electrode buffer (0.025M Tris, 0.2M glycine and 0.1% SDS) at a constant current of 70 mA for 2.5 hours at 10°–15° C. The LOS bands were visualized by silver staining (Bio-Rad silver stain kit).

III. Antibodies (a) Production of idiotype antibody (Ab1) hybridoma cells

The hybridoma cell line that produces mAb 2C7 (Ab1), is an IgG3λ that is directed against an epitope widely expressed in vivo by N. gonorrhoeae. It was prepared by fusion of the mouse myeloma cell line Sp2/0-Ag14 to spleen cells obtained from a Strain A mouse which had been immunized with whole gonococcal outer membranes. Individual cells, secreting antibodies directed against the OS epitope of gonococcal LOS, were subcloned by limiting dilution, and subsequently stored in liquid nitrogen (36).

A frozen vial of the 2C7 cell line was removed from liquid nitrogen (on dry ice) and thawed by warming manually as quickly as possible. When the cells were almost thawed (i.e., with a little ice remaining), the outside of the vial was wiped with 70% ethanol before removing the cap. Cells were transferred to a 15 ml centrifuge tube, containing 10 ml of ice cold Iscove's medium (Iscove's modified Dulbecco's medium containing 4 mM L-glutamine, 5 μg/ml gentamicin and 10% fetal bovine serum) and centrifuged gently (200×g) for 5 minutes. The supernatants were removed and the cells resuspended in 10 ml of fresh ice-cold Iscove's medium. After mixing gently, the cells were transferred to 2 wells of a 6-well tissue culture plate and incubated at 37° C. in a 5% $CO_2$ incubator. After the cells were grown to confluent monolayers, they were diluted 1:10 and again allowed to grow to confluency. Antibody production was checked periodically to confirm that the cells maintained their ability to produce antibody.

Two ml of $10^8$ mAb 2C7 secreting cells, was added to a 162 $cm^2$ tissue culture flask containing 150 ml of fresh Iscove's medium and incubated at 37° C. (5% $CO^2$) until the hybridomas died. At this time, supernatants contained maximum concentrations of antibody. Cell debris was removed by centrifugation (1000×g) for 10 minutes, and the supernatants were stored at −20° C. (100 mls/flask). Antibody was later purified from these supernatants (Section III b).

Some of the viable antibody producing cells were washed twice by centrifuging (2000×g; 4° C.) and resuspending them in Hanks balanced salt solution containing $Ca^{2+}$ and $Mg^{2+}$ ions ($HBSS^{++}$) (Sigma). These cell pellets were resuspended in $HBSS^{++}$, at a concentration of $10^5$ viable cells/0.5 ml. These cell suspensions were used to immunize mice to produce anti-idiotypic antibody (Ab2) (Section IV a).

(b) Purification of idiotypic antibody 2C7 (Ab1)

Approximately 100 ml of frozen mAb 2C7 (IgG3λ) supernatant was thawed to room temperature. An equal volume of 0.1M Phosphate buffer pH 7.0 (PBS) was added, and the mixtures applied slowly (10 mls/hr) to a 5 ml anti-mouse IgG3-agarose column (Sigma, St. Louis, Mo.). These columns have the capacity to bind 0.4 mg (minimum) of mouse IgG3/ml of antibody-agarose. After the supernatants were applied, the columns were washed with PBS until the $OD_{280}$, of the fall through fractions, reached zero. Bound antibody, was then eluted from the column with 0.1M glycine-HCl (pH 3.0). To preserve antibody activity, the pH of the eluted fractions was neutralized immediately by collecting eluent fractions of antibody in tubes containing equivalent volumes of 0.2M Tris-HC1 (pH 8.0) in 0.5M NaCl. Fractions with $OD_{280}$ readings above background, were combined and concentrated to 0.5 mg protein/ml, using a Centricon 30 microconcentrator (Amicon; Beverly, Mass.), dialyzed against normal saline, and filter sterilized. 100 μl aliquots were stored at −20° C. This antibody was used in ELISA assays to screen hybridomas for Ab2 production, and in functional assays, such as the bactericidal assay and the opsonophagocytosis assay.

(c) Biotinylation of Ab1

Purified mAb 2C7 (IgG3λ) was labelled with biotin (NHS-LC-biotin; Pierce, Rockford, Ill.). Briefly, purified antibody (Section III b) was dialyzed against 50 mM Bicarbonate buffer (pH 8.5), using 75,000 MW cutoff collodion bags (Schleicher and Schuell, Keene, N.H.). Dialyzed antibody was transferred on ice to 16×125 mm glass test tubes and biotin was added at a ratio of 1.7 nmol biotin/1 molecule of IgG. This ratio was predetermined, using methods described by Hnatowich et al. (22) and Green (19).

The reaction mixtures were incubated on ice for 2 hours. To remove free biotin, the mixtures were centrifuged (1000× g) two times (30 minutes each), using a Centricon 30 microconcentrator. The sample was washed with 0.1M phosphate buffer pH 7.0, and centrifuged again in the Centricon 30. After dilution, biotinylated antibody was removed from the Centricon 30 and stored at −20° C. in 50 μl aliquots.

(i) Direct ELISA assay

A direct ELISA (Enzyme Linked Immuno Sorbent Assay) was used to test the biotin labelled mAb 2C7 for retention of binding specificity to LOS and to detect the presence of biotin on the antibody. Ninety-six well Immulon U-bottom polystyrene microtiter plates were used for all ELISA assays (Dynatech; Chantilly, Va.). Microtiter wells were coated with 100 μl of a 1/200 dilution of whole gonococci in carbonate buffer (1.59 g $Na_2CO_3$, 2.93 g $NaHCO_3$, 0.2 g $NaN_3$ dissolved in 1 liter distilled deionized water, pH 9.6). The plates were incubated at 37° C. for 3 hours (shaking at 100 rpm), and then stored overnight at 4° C. After removal of residual gonococci (the antigen solution), the wells were washed three times with 200 μls/well of 0.01M PBS with 0.05% Tween 20 (PBS-Tween). The plates were blotted dry on a paper towel and then immersed in a glass dish containing PBS-Tween. A stir bar was placed on top of the plate and stirred (≧30 minutes) at slow speed to rinse the wells with wash solution. Then the plate was blot dried again.

Various dilutions of biotin-labelled and unlabelled antibody (mAb 2C7), diluted in PBS-Tween, were added to the appropriate antigen coated wells and incubated for 1 hour at 37° C. (on a shaker). Plates were washed and dried as above. Next, 100 μl of alkaline phosphatase conjugated anti-mouse IgG or conjugated avidin (diluted 1/1000 in PBS-Tween) was added to the appropriate wells and incubated again for 1 hour at 37° C. (shaking at 100 rpm). Conjugated anti-mouse IgG was used to detect the binding specificity of biotinylated antibody to LOS and conjugated avidin used to detect the presence of biotin on mAb 2C7. Plates were washed and dried as above.

After the final wash, 100 μl of the substrate solution (one p-nitrophenyl phosphate tablet [Sigma 104 substrate tablet] /5 ml of diethanolamine buffer, pH 9.8) was added to each well. Development of color was read at 405 nm, on a Dynatech ELISA plate reader. Measurements were taken at time 0 and the color reaction was allowed to develop at 25° C. for 30 minutes (readings were taken every 5 minutes). Negative controls (each missing one of the components) were included in the plate.

The biotin labelled antibody was later used in ELISA assays to screen hybridomas for Ab2 production.

(d) Monoclonal antibody 2C3 mAb 2C3 (subclass IgG1κ) binds to a highly conserved surface exposed gonococcal lipoprotein epitope, designated H.8 (2). The 2C3 cell line was stored in liquid nitrogen and antibody was produced from the cell line, using the method described earlier for mAb 2C7 production. 2C3 was purified from supernatants using methods substantially similar to those described to purify 2C7, with the exception that anti-IgG1 antibody was used as the ligand on the solid phase instead of an anti-IgG3 (Section IIIa and b). Purified antibody was labelled with biotin (NHS-LC-biotin) according to the procedure described above (Section II c). The biotinylated antibody was stored at −20° C. (100 μl aliquots) and was used later in the opsonophagocytic assay (Section VI [ii]) to detect organisms adherent (but not ingested) on human polymorphonuclear leukocytes (PMNs).

(e) Screening for possible cross-reactivity of 2C7 epitope with major and minor human blood group antigens To assess possible cross-reactivity with major ABO blood group antigens, 24-1 LOS was affixed to solid phase, preincubated with mAb 2C7 followed by incubation with NHS blood typing sera (types A, B or O) and recognition by either anti-human IgG or IgM mAb conjugated to alkaline phosphatase. Next, mAb 2C7 in PBS was incubated with types $A_1$, $A_2$, B or O erythrocytes (type O erythrocytes sensitized with 24-1 LOS were used as a positive control) in a routine hemagglutination assay. Routine typing sera (A and B) were also incubated with LOS-sensitized erythrocytes. The agglutination assays were repeated using erythrocytes which had been pre-treated with trypsin or neuraminidase (37) to expose epitopes obscured by sialic acid.

Possible cross-reactivity of the 2C7 epitope with minor blood group antigens known to cross-react with gonococci was first assessed by ELISA measurement. The carbohydrate sequence specificities of mAbs which bind to both gonococci and human glycosphingolipid antigens are as follows: mAbs 3F11 and 06B4 bind to branched and linear epitopes (formed by Galβ1→4GlcNAcβ1→3Galβ1→4Glc), respectively (36, 37); 3D9 (anti-$P^k$) binds to Galα1→4Galβ1→4Glc-ceramide [cer] (69); 4C8 (gift of M.A. Apicella) binds to GlcNAcβ1→3Galβ1→4Glc; 4C4 binds to Galα1→4Gal (70); SH-34 and 103HT30 bind to asialo-GM1 (Galβ1→3NAcβ1→4Galβ1→4Glc-cer), but 103HT30 does not bind to gonococci (71); and 2D4 to asialo-GM2 (GalNAcβ1→4Galβ1→4Glc-cer) (71). Direct binding of these mAbs to solid phase LOS and whole organisms (strain 24-1, growth both in the presence and absence of CMP-NANA) was measured first. The ability of mAb 2C7 to inhibit binding of those mAbs which bound to either solid phase LOS or whole organisms was subsequently assessed by inhibition ELISA.

IV. Development of anti-idiotype antibody (Ab2)

(a) Murine Immunization with anti-idiotype antibody (Ab2)

Monoclonal anti-idiotype antibody (Ab2) was prepared by immunizing pristane-treated BALB/C mice (Jackson Laboratory, Bar Harbor, Me.) intraperitoneally with $10^5$ hybridoma cells secreting 2C7 mAb (Ab1) (Section III a). Injections were given weekly for 4 weeks. Spleen cells from these immunized mice were used to generate anti-idiotype antibody (Ab2) as described below.

(b) Cell Fusion to generate anti-idiotype antibody (Ab2)

Sp2/0-Ag14 myeloma cells were thawed from liquid nitrogen stocks (as in Section III a) a week prior to the fusion and grown in Iscove's medium supplemented with 10% fetal bovine serum. Myeloma cells were visually monitored by light microscopy to ensure viability and rapid division prior to their use in the fusion assays. One day before the fusion, the cells were fed with fresh medium.

A 35% PEG solution (PEG 4000, American Type Culture Collection, Rockville, Md.) was prepared by melting solid PEG on a hot plate and then cooling it to 37° C. 3.71 ml of pre-warmed sterile Iscove's medium (without serum) was added to 2 grams of sterile PEG. Aliquots of Iscove's with PEG (2 mls/tube) were stored at −20° C. and thawed prior to use.

Thirty-two days after the primary immunization (3 days after the final boost), the immunized mouse (Section IV a) was sacrificed by cervical dislocation. The spleen was removed aseptically and placed in a 10 mm tissue culture dish containing 7 ml of prewarmed PBS. The spleen was teased apart with two sterile forceps until most of the splenocytes were released. The cell clumps were further disrupted by pipetting several times. The resulting cell suspension was transferred to a 15 ml polypropylene centrifuge tube, leaving behind the larger pieces of tissue and cell clumps. Another volume of 7 ml of PBS was added to the remaining clumps and again they were pipetted and combined with the other suspension (14 ml total). After mixing, the cell suspension was allowed to sit for 2–3 minutes to permit settling of large clumps to the bottom of the tube. The suspended cells were carefully removed from the sediment and transferred to another tube. One ml of PBS was added to the remaining sediment and disruption of the clumps was attempted by pipetting. After settling for 2 minutes, this supernatant was removed and added to the 14 ml collected earlier. Next, the entire cell suspension was centrifuged for 10 minutes (250×g) at room temperature and washed twice in PBS. Concomitant with the second wash, myeloma cells (Sp2/0Ag14, prepared above) were collected and centrifuged in a separate tube. In a third wash, the spleen cells and the myeloma cells were washed separately in Iscove's medium (without serum). An aliquot of spleen cells and myeloma cells which had been removed before the final wash and spin were counted.

Approximately $10^8$ spleen cells were resuspended in 10 ml of fresh medium to which $10^9$ myeloma cells were added for a 10:1 ratio of myeloma:spleen cells. The cell mixture was centrifuged (250×g) for 5 minutes at room temperature and the medium was decanted (removing as much media as possible). Two ml of 35% PEG (at room temperature) was mixed into the cell suspension, over 2 minutes. The cells were centrifuged (500×g) for 3 minutes at room temperature and were allowed to stand for 3 minutes without removing the supernatant. Fifty ml of Iscove's medium (without serum) was added slowly to the cells, gently mixed (to dilute PEG) and centrifugeted (250×g) for 5 minutes at room temperature. The supernatant was carefully aspirated and the cells were resuspended in 60 ml of Iscove's medium supplemented with 15% fetal bovine serum (FBS) and HT (100 μM hypoxanthine and 16 μM thymidine). Cells were transferred to 60 wells (two 48-well flat bottom tissue culture plates), in 1 ml aliquots and incubated at 37° C., in a 7% $CO_2$ incubator. At 24 hours, 1 ml of medium supplemented with 15% FBS and HAT (100 μM hypoxanthine, 0.4 μM aminopterin and 16 μM thymidine), was added to each well. Cells were examined twice weekly, for 2 weeks and 50% of the media was replaced with fresh media, supplemented with HAT. After 2 weeks, the cells were fed twice weekly, replacing 50% of the spent media with medium containing HT. Then cells were weaned off HT completely and were grown in Iscove's medium (without HAT or HT). Cell supernatants were screened for production of anti-idiotype antibody (Ab2), 14 days post fusion.

(c) Screening of anti-idiotype antibody (i) Immunodot assay

Supernatants from antibody-producing hybridoma cultures were screened initially for anti-idiotype (Ab2) by an immunodot assay (21). Immobilon PVDF membranes (Millipore) were pre-treated in methanol for 2 seconds, washed with deionized and distilled water for 2 minutes, then placed in 0.7% acetic acid for 30 minutes. A capillary spotting station was prepared by placing 2 layers of wet filter paper on top of several layers of dry paper towels. The wet membranes were placed on top of the filter paper, removing air bubbles between the membranes and the filter papers. Fifty μl of the supernatants were applied to membrane surfaces as small dots. LOS antigen, diluted in PBS (20 μg/50 μl), was used as a positive control. Fifty μl of media and 50 μl of supernatant from non-antibody producing cells were used as two negative controls. These controls were applied to the membranes in a similar fashion. Membranes were washed and developed according to the procedure of Blake et al. (3). Briefly, membranes were incubated in blocking buffer (PBS containing 0.5% Tween 20) for 2 hours at room temperature. This was followed by placing the membranes in a solution of biotin-labelled antibody 2C7 (Ab1) (Section III c), diluted 1/500 in 1% BSA-PBS containing 0.5% NaCl. Membranes were incubated overnight at 4° C. on a to-and-fro shaker (100 rpm) and were then washed by placing them three times in fresh blocking buffer, for 5 minutes each time at room temperature. Next, the membranes were incubated in a 1/1000 dilution of alkaline phosphatase labelled avidin (Sigma) in 1% BSA-PBS, for 2 hours at room temperature, on a shaker and then washed three times in blocking buffer and once with 0.15M Veronal acetate buffer (pH 9.6). Stock solutions for the alkaline phosphatase substrate were made as follows: 5-bromo-4-chloro indoxyl phosphate (5 mg/ml) in dimethylformamide (US Biochemicals Corp, Cleveland Ohio), NBT (1 mg/ml in Veronal acetate buffer (US Biochemicals Corp) and 2M $MgCl_2$. 20 µl of $MgCl_2$, 1 ml of 0.1% NBT, 0.1 ml of indoxyl phosphate and 9 ml of Veronal acetate buffer were mixed and added to the washed membrane and incubated at room temperature, on a shaker, until color developed. The reaction was stopped by washing the membranes with deionized and distilled water.

(ii) Isotyping assay

A mAb-based isotyping system for mouse immunoglobulins (Gibco BRL) was used to isotype cell supernatants that screened positive for anti-idiotype (e.g., they were positive in the immunodot assays above). The assay was performed according to the instructions provided by the manufacturer. All the reagents were provided in the kit. The assay was performed as follows.

Anti-mouse isotype specific antibody (i.e., anti-IgGI, anti-IgG2$a$, anti-IgG2$b$, anti-IgG3, anti-IgM, and anti-IgA) and antisera specific for the immunoglobulin light chains (κ and λ) were diluted 5 fold in 50 mM Tris, 200 mM NaCl (pH7.5) (TBS). Fifty µl of the above antibody dilutions, were added to wells of U-bottom, 96-well Immulon I plates (Dynatech). Plates were incubated for 1 hour at 37° C., washed 4 times with TBS, containing 0.05% Tween 20, and blotted dry on paper towels. 50 µl of blocking buffer (1% BSA in TBS) was added to each well and incubated for 15 minutes (37° C.). Plates were washed and dried as above, and 50 µl of the supernatant samples were added to the appropriate wells. Fifty µl of a positive and a negative control, were added to the appropriate wells. Plates were incubated for 1 hour (37° C.), washed, and dried as above. Fifty µl of alkaline phosphatase-conjugated rat anti-mouse Ig was added to each well and incubated for 1 hour (37° C.). Plates were washed and dried; 50 µl of substrate solution (10% [w/v] diethanolamine [pH 9.8], 0.5 mM $MgCl_2$, 0.02% [w/v] sodium azide; provided in the kit) was added to each well and incubated for 30 minutes (37° C.) The wells were examined for a color reaction, using a Dynatech ELISA reader. If the cell supernatant contained mAbs of a particular isotype, a color reaction was detected. The optical densities ($OD_{405}$) of the samples were compared to the positive and negative controls.

(iii) Competitive ELISA

Individual wells of a U-bottom, 96-well Immulon I plate (Dynatech; Chantilly, Va.) were coated with 100 µl of LOS (80 µg/ml) prepared from 24-1 gonococci (Section II a) diluted in barbital acetate buffer (pH 4.6)(34). The plate was incubated overnight as described above (Section III c [i]).

The following day, dilutions of supernatants (in PBS-Tween 20) from anti-idiotype antibody (Ab2) producing cells were mixed with a fixed amount of biotin-labelled Ab1 (Section III c), in a 12×75 mm glass test tube, and incubated at 37° C., in a shaking water bath for 1 hour to saturate the binding sites on Ab1. The amount of biotin labelled Ab1 used (when detected with alkaline phosphatase labelled avidin) was predetermined, as that dilution that gave an $OD_{405}$ reading of approximately 0.4 after 30 minutes (at room temperature).

The plate was washed and dried (as in the direct ELISA assay). One hundred µl of the Ab1:Ab2 mixture was added to the wells and incubated for 1 hour at 37° C., on a shaker. After removing residual Ab1:Ab2 mixture, 100 µl of alkaline phosphatase-labelled avidin (Sigma) (1/1000 in PBS-Tween) was added. Plates were incubated for 1 hour at 37° C. on a shaker and then, washed and dried. 100 µl of substrate solution (one tablet of p-nitrophenyl phosphate [Sigma 104 substrate tablet]/5 ml of diethanolamine buffer, pH 9.8) was then added to each of the wells. The color reaction was read at $OD_{405}$ on a Dynatech ELISA plate reader as described above. (Section III c [i]). The color intensity in the reaction mixtures were compared to the uninhibited control (unabsorbed Ab1), which was included on each plate.

(iv) Displacement ELISA

In this assay, a fixed amount of biotin labelled, mAb 2C7 (Ab1) was added to 24-1 gonococcal LOS coated wells and incubated for 1 hour (37° C.) on a shaker. The plates were washed and dried as described above (Section IV c [iii]). One hundred µl of anti-idiotype (Ab2) supernatants, diluted in PBS Tween 20, were added to appropriate wells to displace the conjugated mAb 2C7. The plates were incubated, washed, and dried as above and the reaction developed as described in Section IV c (iii).

(d) Cloning of hybridomas (i) Soft agarose cloning

Ab2-secreting hybridoma cells (identified by screening supernatants by immunodot, competitive and displacement assays) were cloned as follows. Three percent agarose (Sigma) solution was prepared in endotoxin free, sterile water (Sigma), autoclaved for 30 minutes, and then cooled to 42° C. in a water bath for 5 minutes. This agarose solution remains stable for 6 months and may be microwaved for future use. Iscove's medium, supplemented with 20% fetal bovine serum (FBS) and 10% Origene® Hybridoma Cloning Factor (Igen, Inc., Rockville, Md.) (42° C.), was added to the agarose to a final concentration of 0.3% agarose. Five ml aliquots were added to sterile 60 mm tissue culture dishes, allowed to solidify at 4° C., and then moved to a 37° C., 5% $CO_2$ incubator for at least 30 minutes.

The hybridoma cells were harvested from culture plates and resuspended in Iscove's media to a final concentration of 10,000 cells/ml. One hundred µl aliquots of the cell suspensions were added to 1 ml of the 0.3% agarose media (prepared above; 42° C.). One ml of the cell-agarose-media solution (containing approximately 1000 cells), was pipetted dropwise quickly in a circle on top of a tissue culture dish containing 5 ml of the solidified 0.3% agarose. At least 5 dishes were prepared from each cell suspension. The dishes were quickly moved to a 4° C. work space and the top cell-agarose-media layer was allowed to solidify for 5 minutes before moving the dishes to a 5% $CO_2$, 37° C. incubator. Microscopic clones appeared after 3–5 days. Individual clones were picked with a sterile pipette, transferred to 100 µl of medium in a 96 well tissue culture plate, and incubated at 37° C. for 3 days. Supernatants from each well were screened for antibody production by isotyping ELISA (Section IV c [ii]). The antibody producing cells, with high titers of antibody were grown in larger volumes and checked for specific antibody production, in competitive and displacement ELISAS. These cloned hybridoma cells were stored in liquid nitrogen by slowly freezing them in tissue culture media containing 10% dimethylsulfoxide (DMSO).

(e) Purification of Ab2

Purification of monoclonal anti-idiotype antibody Ab2 (in this case IgM) employed the same method used to purify Ab1 (Section III b) except that an anti-mouse IgM bound to agarose was used for immunopurification. The purified antibody was used to produce anti-anti-idiotype antibody (Ab3).

(f) KLH Conjugation of Ab2

Purified monoclonal anti-idiotype antibody (Section IV e) was coupled to keyhole limpet hemocyanin (KLH) with glutaraldehyde, according to the procedure described by Mishell et al. (38). Purified anti-idiotype antibody (1.4 mg) (Ab2; 0.5 mg/ml of 0.9% NaCl), was dialyzed against approximately 100 ml of 0.1M Phosphate buffer (pH 6.8) then mixed with KLH at a ratio of 0.5 mg antibody to 2.5 mg of KLH. Ten µl of aqueous 0.5% glutaraldehyde (fresh) per 0.5 mg of antibody was slowly added to the mixture and allowed to react for 1 hour at room temperature. The reaction was terminated by dialyzing against approximately 100 ml of 0.1M $(NH_4)_2CO_3$ for 3–4 hours at 4° C., followed by overnight dialysis against 100 ml of 0.05M phosphate buffer (pH 7.5). Precipitates (if any) were removed by centrifugation at 10,000 rpm for 15 minutes. The supernatant was applied to a Sepharose C1-2B column (1×40 cm) equilibrated in 0.05M Phosphate (pH 7.5), and 2 ml fractions were collected. The first peak, which includes the Ab2-KLH, was pooled and concentrated back to the original volume using a Centricon 30 microconcentrator. Fifty µl aliquots were stored at −20° C. This material was used for immunizing rabbits to develop anti-anti-idiotype antibodies (Ab3) (Section V b).

24-1 gonococcal LOS (500 µg), Group C meningococcal capsular polysaccharide (C-MCP) (500 µg), and an irrelevant IgMκ mAb (Sigma) (1.5 mg) were also conjugated with KLH, as above. 24-1 LOS and C-MCP were concentrated to 1 ml using Centricon 3 microconcentrators and irrelevant IgMκ mAb was concentrated to 2 ml using a Centricon 30 microconcentrator. These KLH conjugated preparations were used to immunize control rabbits (Section V b).

V. Development of anti-anti-idiotype antibody (Ab3)

(a) Immunization of syngeneic mice for Ab3 production

Anti-anti-idiotype antibody (Ab3) was elicited in 12 week old syngeneic BALB/c mice (Jackson Laboratory, Bar Harbor, Me.) by intraperitoneal (ip) injections of purified Ab2 (1, 10, 100, or 200 µg) in 0.5 ml sterile PBS. Control mice were immunized with either sterile PBS, 10 µg of irrelevant IgMκ mAb, or 10 µg of 24-1 gonococcal LOS. The 10 µg dose was used to immunize four mice, one animal was used for each of the remaining immunogens. Booster immunizations were given ip 2 weeks later with the equivalent dose of the original antigen. Mice were tail-bled weekly beginning on day 0. Their sera were tested in an ELISA (Section V c (i)).

(b) Immunization of xenogeneic rabbits for Ab3 production

Six week old New Zealand white rabbits (Pine Acres Farm, Mass.) were immunized subcutaneously (sc) with purified Ab2-KLH (5, 10, 50, or 100 µg) suspended in complete Freund's adjuvant (CFA) (2 ml of immunogen:2 ml CFA), at 10 different sites (400 µl/site) on days 0 and 14. Intravenous (iv) injections (of equivalent dose; without KLH or CFA) were given on day 42 and sc (of equivalent dose; with KLH in CFA) on weeks 28, 30, and 32. The rabbits receiving 10 µg and 100 µg doses of CA1 were boosted iv with 50 µg of Ab2 on week 60.

Control rabbits were immunized, as above, with either 100 µg of 24-1 gonococcal LOS, 100 µg of irrelevant monoclonal murine IgMκ or 100 µg of group C meningococcal capsular polysaccharide (C-MCP) (all coupled to KLH and suspended in CFA). Rabbits were bled weekly during the first 7 weeks (via ear artery) and then prior to each boost. Sera were tested in an ELISA (Section V c [i]).

(c) Screening of Ab3 antibodies (i) Enzyme Linked Immuno-Sorbant Assay (ELISA)

Pre- and post-immunization sera from the mice and rabbits (Section V a&b) were tested by ELISA for anti-anti-idiotype (Ab3) production. U-bottom, 96 well Immulon I plates were coated (as in Section III c [i]) with 100 µl of 24-1 gonococcal LOS (80 µg/ml) in Barbital acetate buffer, pH 4.66 (10). Plates were washed and dried. Sera dilutions (in PBS-Tween 20) were added to the microtriter wells and incubated for 1 hour at 37° C., on a shaker. After washing and drying the plates, 100 µl of a 1/1000 dilution of alkaline phosphatase conjugated to goat anti-mouse IgG (or IgM) or alkaline phosphatase conjugated to goat anti-rabbit IgG (or IgM) was added to the appropriate wells and incubated for 1 hour at 37° C. on a shaker. After washing and drying, 100 µl of the substrate solution was added to each well and the color development was read (as described in Section III c [i]).

VI. Functional activity of Ab1 and Ab3

(a) Preparation of Complement

Complement was prepared according to the method described by Joiner et al. (23), using commercially available fresh normal mouse serum (SIGMA) and fresh normal rabbit serum (Gibco) as the complement source in the bactericidal assays. Fresh blood, drawn from C5 deficient B10.D20SNJ mice (The Jackson Laboratory, Bar Harbor, Me.), was used as the complement source in the opsonophagocytic assays by initially allowing it to clot at room temperature for 15 minutes; centrifuging at 3000×g (10 minutes) and immediately placed in an ice bath.

Organisms were streaked onto chocolate agar plates and incubated overnight in a 37° C., 5% $CO_2$ atmosphere (candle extinction jar). They were harvested with a cotton tipped swab into 1 ml 0.1M PBS by centrifugation. The organisms were incubated in 1 ml of 0.25% glutaraldehyde in PBS for 30 minutes at room temperature and washed as above. 1 ml of DL-Lysine (1 mg/ml of PBS) was then added to the organisms (to quench the residual glutaraldehyde) for 20 minutes at room temperature. The organisms were washed (as above), added to 5 ml of serum and rotated end-over-end for 1 hour (4° C.). The sera were centrifuged (3000 ×g) for 10 minutes at 4° C. (to remove the organisms) and filter sterilized through a 0.22 µm Millipore filter. The sera (complement source) were stored at −70° C. Aliquots, absorbed with the organisms used in the assay, were thawed and used immediately in the assays (Section VI d).

(b) Propagation of organisms

Media used in growing the Neisseria organisms was prepared according to methods described by Morse et al. (39).

Solution A was prepared by dissolving 1.5 g protease Peptone #3, 0.4 g potassium phosphate (dibasic), 0.1 g potassium phosphate (monobasic), 0.5 g sodium chloride and 0.1 g soluble starch in 100 ml deionized and distilled water. It was autoclaved for 15 minutes, cooled to room temperature and stored at 4° C. for 2 weeks. Solution B was prepared by dissolving 0.042 g sodium bicarbonate and 4.0 g glucose in 90 ml deionized and distilled water, filtered sterilized (0.22 µm Millipore filter), and stored at 4° C.

One loopful of thawed organisms (obtained from a frozen culture stock, stored at −70° C.) was transferred to a chocolate agar plate and incubated for 14–16 hours at 37° C. in a 5% $CO_2$ atmosphere (candle extinction jar). Pure colonies were streaked onto a second chocolate agar plate to obtain a solid lawn of organisms. Plates were incubated as above. In the experiments that required sialylated organisms, gonococci were grown on chocolate agar plates, containing 1 ml of 80 µg of the ammonia salt of 5'-cytidinemonophospho N-acetyl neuraminic acid (CMP-NANA) (SIGMA).

After incubation, the organisms were collected into 1 ml of Solution A and mixed thoroughly. The bacterial suspension was added (until $OD_{650}$=0.1) into a sterile sidearm flask containing 9 ml of Solution A, 1 ml of Solution B and 0.1 ml of a mixture of vitamins, amino acids and dextrose formulated so that it was identical to a commercially available product called Isovitalex®. Again, if sialylated organisms were needed, CMP-NANA (80 µg/ml) was added to the liquid growth media. The culture was allowed to grow at 37° C., with vigorous stirring, to create aeration to a mid log phase concentration of approximately $10^8$ CFU/ml ($OD_{650}$= 0.2).

These organism suspensions were used in bactericidal (Section VI c) and opsonophagocytic assays (Section VI d) described below.

(c) Bactericidal assay

The bactericidal assay method used was a modification (27) of procedures described by Roberts (47) and Gold and Wyle (55) for N. meningitidis. Bacterial cultures ($10^8$ CFU/ml, OD=0.2) were prepared as described above and diluted 400 fold with Solution A to obtain approximately $10^5$ CFU/ml. The tube was incubated in a 37° C. rotary shaker water bath until used (maximum 10 minutes).

Reaction mixtures were set up in 12×75 mm sterile polystyrene tubes with caps. Each test mixture contained 0.025 ml of diluent (Gey's balanced salt solution), 0.025 ml of the bacterial suspension, 0.05 ml of the test antibody [serial antibody dilutions of Ab1 (2C7) or Ab3, or control antibodies prepared in animals immunized with LOS or C-MCP] (Section III[b], V[a] and [b]) and 0.05 ml of the absorbed complement source (Section VI a). After vortexing, 0.025 ml of the mixtures were inoculated onto duplicate chocolate agar plates and spread evenly with a flamed glass rod to obtain the number of colony forming units (CFUs), at time 0. The mixtures were then incubated at 37° C. in a rotary shaking water bath for 30 minutes. Aliquots of 0.025 ml of the reaction mixtures (at time 30 minutes) were again inoculated onto another set of duplicate chocolate agar plates and spread as above. The plates were incubated at 37° C. in 5% $CO_2$ atmosphere (candle extinction jar).

CFUs were counted using a Quebec Colony counter. Killing was expressed as the percent decrease in colony count at 30 minutes, compared to the 0 minute.

As a positive control for the presence of adequate complement activity, a serum with known bactericidal activity against the bacterial test strain was used. Negative controls included active complement without the test serum and a reaction mixture containing heat inactivated (56° C. or 30 minutes) complement and test serum.

(d) Opsonophagocytic assay

The opsonization of organisms and the phagocytic assay used was a modification of procedures described by Sveum et al. (55), and Ross and Densen (48).

(i) Preparation of PMNs

Polymorphonuclear leukocytes (PMNS) were prepared according to the procedure described by the manufacturer of Polymorphprep™ (13.8% Sodium Metrizoate and 8% Dextran 500) (Nycomed Pharma As, N-0401, Oslo 4, Norway). Briefly, 30 ml of whole blood were drawn from normal adult human volunteers and immediately transferred to a 50 ml centrifuge tube containing 45–50 mg of EDTA dipotassium salt and mixed gently. Approximately 5 ml of the anticoagulated whole blood were carefully layered over 3.5 ml of Polymorphprep™ in a 15 ml centrifuge tube. The tubes were centrifuged (500×g, for 30 minutes) in a swing out rotor, at room temperature. The serum (top layer) and the cell band at the interface consisting of mononuclear cells were carefully removed without disturbing the lower PMN band. PMNs were transferred to another 15 ml centrifuge tube and diluted with an equal volume of 0.45% NaCl. They were centrifuged (500×g, for 10 minutes at 4° C.) and washed twice with sterile 0.1M PBS at 4° C. If the PMNs appeared contaminated with erythrocytes (pink color), 1 ml of cold sterile water was added to the cells for 30 seconds (to lyse the erythrocytes), then PBS was added for a total volume of 14 ml and centrifuged as above. The final cell pellet was resuspended in 1 ml of PBS and the cells were counted using a hemocytometer. The suspension was diluted with PBS for a final concentration of $2 \times 10^7$ PMNs/ml and kept on ice and used within 30 minutes.

(ii) Opsonization of the organisms $10^8$ CFU/ml ($OD_{650}$=0.2) of the bacterial test organisms (Section VI b) were used in this assay. Eight ml of bacterial culture (from a total of 10 ml) were centrifuged in a microcentrifuge and washed twice with Hank's balanced salt solution containing $Ca^{2+}$ and $Mg^{2+}$ ions ($HBSS^{++}$) (Sigma). The pellets containing approximately $5 \times 10^8$ organisms, were resuspended in 0.5 ml of 0.1M $NaHCO_3$ (pH9.5). 0.5 ml of Lucifer yellow (Sigma) (2 mg/ml in 0.1M $NaHCO_3$, pH9.5) was added to the suspension and rotated end-over-end for 45 minutes at room temperature. The organisms were washed thrice in $HBSS^{++}$ (as above) and resuspended in $HBSS^{++}$ at a concentration of $5 \times 10^8$ organisms/ml. Opsonizing antibody [either mAb 2C7 (Ab1) (Section III a) or rabbit pre- or 14 days post-sera (Ab3) (Section V b) were added to 250 µl of the organism suspension to produce a final antibody dilution of 1/100 for mAb 2C7 and 1/500 for rabbit sera. This mixture was then incubated for 30 minutes at 37° C. in a rotary shaking water bath. In a separate tube, 250 µl of the organism suspension without opsonizing antibody was incubated as a negative control. After 30 minutes of incubation the organisms were washed thrice in $HBSS^{++}$ (as above) at room temperature. The opsonized organisms were resuspended to a concentration of $5 \times 10^8$ cells/ml in $HBSS^{++}$, and incubated on ice for about 5 minutes prior to use in the phagocytic assay.

For a negative staining control, the remaining 2 ml of organisms (from the original 10 ml culture) were fixed with 0.5 ml of Haema-line 2® (Serono-Baker Diagnostics, Allentown, Pa.) containing 1% paraformaldehyde and kept on ice until analyzed. Also, an aliquot of stained organisms was fixed in a similar fashion.

(iii) Phagocytic assay

Adherence

Opsonized (test) and non-opsonized (control) organisms ($2.5\times10^7$ cells/50 μl of HBSS$^{++}$) were allowed to adhere to PMNs ($10^6$ cells/50 μl of HBSS$^{++}$) in separate reaction tubes. In experiments that used complement, ten percent (10 μl) complement (prepared in Section V a) was added to the organisms, prior to the addition of PMNs. The mixtures (at a ratio of 25 organisms/PMN) were incubated for 30 minutes at 0° C. (to permit adherence without internalization). One ml of ice cold HBSS$^{++}$, supplemented with 1% BSA, was added to the tubes. Unbound organisms were separated from the PMNs by centrifugation (250×g, for 5 minutes, at 4° C.). Each pellet, containing PMNs with adherent organisms, was resuspended in 100 μl of ice cold HBSS$^{++}$ with 1% BSA, aliquotted into prechilled 12×75 mm sterile polystyrene tubes (25 μλ/tube), and kept on ice.

Phagocytosis

Three 25 μl aliquots of PMNs, with adhered organisms (opsonized or nonopsonized), were incubated at 37° C. in a rotary shaking water bath. These conditions allowed the PMNs to ingest the organisms. The phagocytic reaction was stopped by adding 42 μl of ice cold HBSS$^{++}$ supplemented with 1% BSA, to one tube every 10 minutes, and placing it into an ice bath.

Counterstaining

After phagocytosis, PMNs were incubated for 30 minutes with 50 μl of ice cold biotin-labelled mAb 2C3 (0.5 μg/ml) (Section III d). mAb 2C3 will only bind to the bacterial organisms on the surface of the PMNS. One ml of HBSS$^{++}$ supplemented with 1% BSA, was added to each tube and centrifuged (1500×g) for 10 minutes. The cells were washed by suspending them in 1 ml HBSS$^{++}$, supplemented with 1% BSA, and centrifuged as above. The cell pellets were incubated with 1.5 μg (6 μl) of Streptavidin Phycoerythrin (PE)-Texas red (SAPETR) (Gibco) on ice, for 30 minutes. The cells were then washed (as above). Next, the PMN/organism pellets were fixed with 0.5 ml of Haema-line 2® containing 1% Paraformaldehyde and stored on ice until analyzed.

For the SAPETR staining control, Lucifer yellow stained, non-opsonized and nonphagocytized, organisms were incubated with biotin labelled mAb 2C3 and processed as indicated above.

Flow cytometry

Flow cytometric analysis, of the fixed PMNs, was performed on a single Argon-ion laser FACS (Becton Dickinson, FACS systems, Sunnyvale, Calif.). Lucifer yellow (green fluorescence) excites at 488 nm and emits at 520 nm [detected in the Fluorescence 1 (FL 1) channel]. Phycoerythrin excites at 488 nm and emits at 575 nm, which in turn excites the adjacent Texas red. Texas red (red fluorescence) then emits at 618 nm [detected mostly in the Fluorescence 3 (FL 3) channel].

The increase in fluorescence emission, in FL 1 and FL 3, were expressed as the mean fluorescent channel (the average intensity of fluorescence emitted by 10,000 cells). The intensity of fluorescence is directly correlated with the mean fluorescence (16). The higher mean fluorescence measurements, indicate larger numbers of organisms adhered to PMNs (13, 54).

As phagocytosis occurs, less gonococci will be available to bind biotinylated mAb 2C3 and therefore less SAPETR will bind (i.e., less emission in FL 3), while the total number of organisms present should remain constant (constant emission in FL 1).

Results

I. Characterization of primary antigen (LOS)

The purity of the LOS antigen and lack of recognizable protein contamination was confirmed by SDS-PAGE. Most strains of gonococci produce from 1–6 antigenically and structurally distinct LOSs that migrate on SDS-PAGE as subunit molecular masses ranging between 3200–7100 MW. LOS prepared from the serum sensitive strain 24-1 by 45% hot phenol extraction migrated faster than the 14.4 KD standard market on SDS-PAGE. No higher MW protein bands were visualized on the gel.

II. Antibody (a) Production and purification of idiotype antibody 2C7 (Ab1)

Idiotype MAb 2C7 (Ab1) was produced from the 2C7 hybridoma cell line and was purified from tissue culture supernatants (26).

Enrichment and concentration of mAb 2C7 (Ab1), identified as an IgG3A subtype, was accomplished by affinity chromatography. One hundred mls of hybridoma cell supernatant were applied to an agarose lined anti-mouse IgG3 affinity column. Peak fractions were pooled and concentrated to 0.5 mg/ml with a Centricon 30 microconcentrator, dialyzed against normal saline, and filer sterilized. Aliquots (100 μl) were frozen at −20° C. Attempts to concentrate antibody to higher concentrations (i.e., >1 mg/ml), produced precipitation and loss of antibody binding activity in direct ELISA assay.

(b) Characterization of idiotype antibody 2C7 (AB1) reactivity with human blood group antigens Some anti-LOS MAbs (3F11 and 06B4) are known to recognize human blood group precursor antigens (37). This structural similarity of LOS epitopes on N. gonorrhoeae to human erythrocyte precursors is significant in several aspects of the pathogenesis of gonococcal infection. First, antigenic similarity may allow the organism to mimic the surface structure of the host, thus facilitating attachment and adherence to host surfaces and phagocytic cells. This may also play a role in the specificity of the gonococcus for human genital epithelial cells. Second, antigenic mimicry may allow the organism to appear like a "self" surface and subvert normal humoral and cellular immune responses. This antigenic similarity is particularly important in the consideration of LOS-derived OS epitopes as vaccine candidates, where presentation of a "self" antigenic stimulus could lead to either no response or, more importantly, to the production of an autoimmune response.

Therefore, the possibility that MAb 2C7 might recognize human erythrocyte GSL antigens was assessed by inhibition ELISA (14). NHS was taken from donors with blood types A,B, or O. Blood type was defined by (i) the presence of antibodies that agglutinated the heterologous red blood cells and (ii) the ability of blood group-specific MAbs to correctly identify the donor red blood cells by agglutination. In these experiments, LOS prepared from our SS prototype strain named 24-1 (121) was coated to microtiter plate wells. Varying dilutions of MAb 2C7 were added to the wells first, followed by NHS incubation and, finally, recognition by either anti-human IgG or IgM-HRP conjugate. No inhibition was demonstrated in four type B sera (shown to have antibody directed against blood group A antigen), three type O sera (antibody directed against A and B antigens), and four type A sera (antibody against blood group B antigen). Furthermore, 2C7 (diluted in PBS) did not agglutinate type A1, A2, B, or O erythrocytes but did agglutinate type O erythrocytes that had been sensitized with SS (24-1) LOS (positive control). None of the sera used agglutinated LOS-sensitized erythrocytes. Taken together, these data suggest that the epitope recognized by MAb 2C7 is not similar to the major human (ABO) blood group antigens.

mAbs which recognize human glycosphingolipid antigens previously shown to cross-react with gonococcal LOS epitopes were next screened against whole gonococci and purified LOS. Subsequently, the ability of mAb 2C7 to inhibit binding of mAbs positive in the direct binding ELISA was assessed. Results indicated no cross-reactivity between 2C7 epitope and previously identified cross-reactive epitopes. Others have demonstrated that mAb 3F11-mediated agglutination of erythrocytes can be increased by both trypsin and neuraminidase treatment to unmask sialylated GSL epitopes (37); however, neither trypsin and neuraminidase treatment caused mAb 2C7 to agglutinate erythrocytes (mAb 2C7 did agglutinate positive control type O erythrocytes that had been sensitized with strain 24-1 LOS). Similarly, ELISA data indicated that pre-absorption of mAb 3F11 with either trypsin- or neuraminidase-treated erythrocytes (compared to pre-absorption with untreated erythrocytes) reduced binding to solid phase 24-1 LOS by approximately 50% and 95%, respectively, while residual binding of mAb 2C7 to LOS was unchanged by absorption. Taken together, these data suggest that the epitope identified by mAb 2C7 does not have antigenic similarity to human glycosphingolipid antigens and thus would not be expected to evoke an autoimmune response.

III. Anti-idiotope antibody (Ab2)

(a) Development of anti-idiotype antibody (Ab2)

Anti-idiotope antibody (Ab2) was produced by intraperitoneal immunization of pristane treated BALB/c mice with hybridoma cells secreting mAb 2C7 (IgG3), followed by fusion of splenocytes with a non-secreting Sp2/0-Ag14 myeloma cell line. After HAT selection, supernatants were initially screened for the production of antibody that binds to biotinylated mAb 2C7 by immunodot assay. The positive supernatants were subsequently used in an isotyping ELISA. One hundred one of 144 supernatants produced IgMκ antibody. We chose 21 wells that contained rapidly growing cells and tested the supernatants in two additional ELISA assays that used 24-1 gonococcal LOS, (bearing the 2C7 epitope) coated to solid phase.

In the first ELISA (competitive ELISA) varying dilutions of Ab2 supernatant were tested for their ability to compete with biotin-labelled mAb 2C7 for binding to LOS. Ten out of 21 supernatants showed >45% inhibition of 2C7 binding to LOS in this assay at ⅛ dilutions of the supernatants. The remaining supernatants showed less (>30% to <45%) inhibition. Two negative controls (media and supernatant from non-antibody producing cells [diluted 1:8]) showed <15% inhibition.

We chose 5 out of 10 supernatants that gave <45% inhibition in the competitive ELISA and tested them in a second (displacement) ELISA.

In the displacement ELISA, we tested the ability of varying dilutions of Ab2 supernatant to displace biotin-labelled mAb 2C7 pre-bound to LOS on solid phase. Four out of 5 supernatants (1:2 dilution) displaced >60% of biotin-labeled mAb 2C7 and one displaced 40%. A negative control (supernatant from non-antibody producing cells [p1:2 dilution]) showed <20% displacement. One of the 5 clones (named CA1), produced large quantities of IgMκ antibody and was further subcloned by the soft agarose method.

After growing and expanding the antibody-producing clone in order to produce a large quantity of antibody we then purified mAb CA1 from the supernatant by affinity chromatography.

(b) Purification of anti-idiotype antibody CA1 (Ab2)

mAb CA1 (IgMκ) was purified from 100 mls of hybridoma cell supernatant using anti-mouse IgM-agarose affinity chromatography. The total protein eluted from the column was about 2 mg in 10 mls. This antibody was concentrated to 0.7 mg/ml in a Centricon 30 microconcentrator. Two mls of this purified antibody was conjugated to keyhole limpet hemocyanin (KLH), as described below.

(c) Conjugation with KLH

Purified anti-idiotype antibody (Ab2), an IgMκ (1.4 mg in 2 mls), was coupled with KLH using glutaraldehyde as a cross linker. Antibodies conjugated to KLH eluted in the first peak from a Sepharose Cl-2B column, which was between 65–78% of the column total bed volume. Fractions comprising the 1st peak were pooled and concentrated back to the original volume.

Two mg of irrelevant IgMκ mAb (commercially available from Sigma), 500 μg of 24-1 LOS and 500 μg of group C meningococcal capsular polysaccharide (C-MCP) were also coupled to KLH for use as controls in the immunization studies. Similar elution profiles were seen on Sepharose Cl-2B gel columns.

IV. Development of anti-anti-idiotype (Ab3)

(a) Immunization of syngeneic mice (BALB/c)

Immunodot and ELISAs (competitive and displacement) assays suggested that mAb CA1 (Ab2) was a molecular mimic of the 2C7 epitope present on the LOS of most gonococcal strains. In order to prove this, we determined whether use of the Ab2 as an immunogen would induce anti-LOS antibody (Ab3) that would recognize the 2C7 epitope. We first performed immunizations in identical strains of mice used to prepare the Ab2 (BALB/c [syngeneic]).

Twelve week old BALB/c mice were immunized intraperitoneally (ip) with varying doses (1, 10, 100 or 200 μg) of purified mAb CA1 (Ab2). The 10 μg dose was used to immunize four mice and one animal was used for each remaining dose. Control immunizations were performed with an irrelevant murine IgMκ mAb, 24-1 gonococcal LOS and PBS. Each mouse was bled prior to and then weekly after immunization, to assay the Ab3 antibody level (determined by binding to LOS in ELISA). Booster immunizations consisted of the same dose of the original antigen given ip at 14 days.

Figure 1:
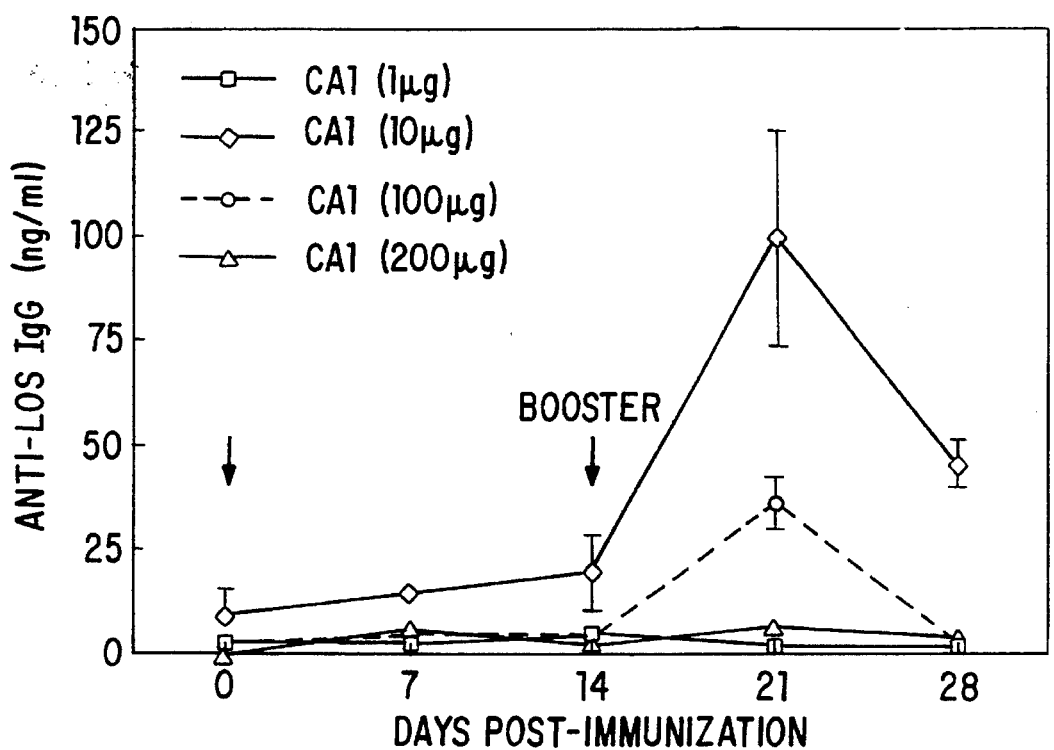
FIG. 1 depicts IgG anti-LOS antibody (Ab3) levels in syngeneic mice immunized intraperitoneally (ip) with varying doses of purified mAb CA1 (Ab2). In the figure, arrows indicate the immunization times.

The 10 and 100 μg doses of mAb CA1 (Ab2) evoked Ab3 (IgG, anti-LOS antibody) responses in the mice that were detected by ELISA (FIG. 1). In the figure, each point represents the mean of 2–4 experiments. There were no Ab3 responses in the mice immunized with either 1 or 200 μg of mAb CA1 (Ab2).

The mice immunized with 10 μg of CA1 developed a 2.5 fold rise at 14 days and booster immunization elicited a rapid antibody production to a level of 12 fold higher than the preimmunization level on day 21 (a week after the booster dose). The mouse immunized and boosted with 100 μg of CA1 developed a 11.7 fold rise at 21 days (FIG. 1).

Figure 2:
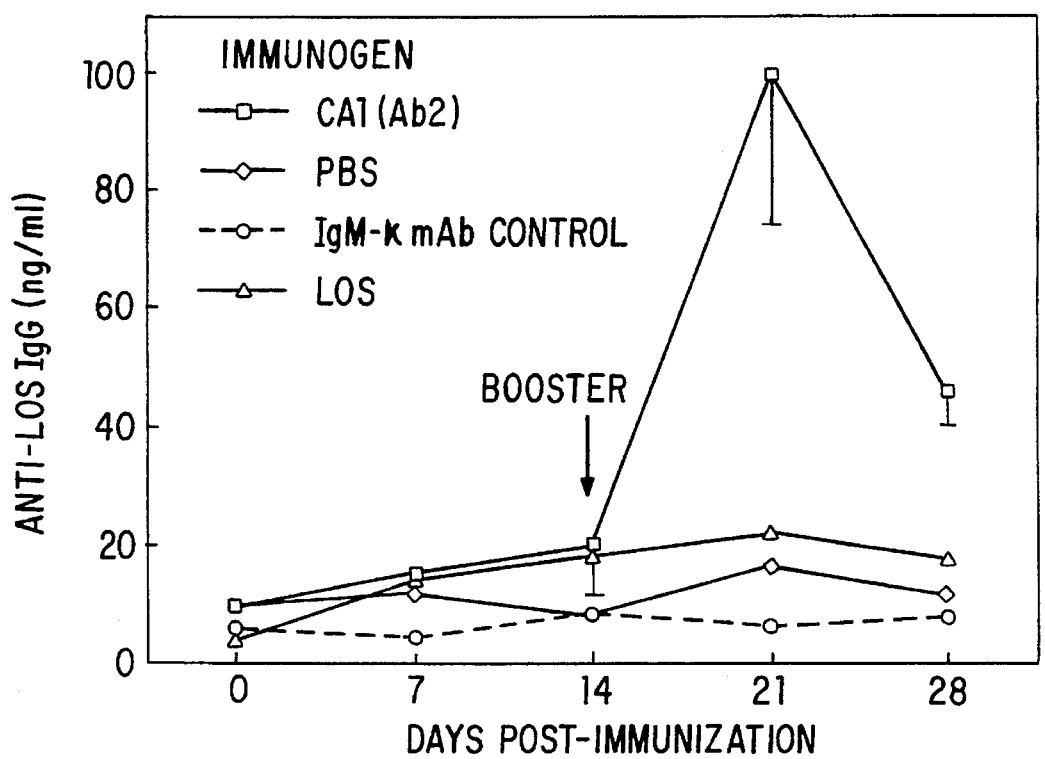
FIG. 2 depicts a comparison of IgG anti-LOS antibody (Ab3) levels in syngeneic mice immunized with mAb CA1 (Ab2), a control mAb of the same isotype as mAb CA1, LOS and PBS. In the figure, the arrow indicates the booster immunization.

The mouse immunized with LOS had a 4.5 fold rise in anti-LOS IgG antibody, on day 21. Control mice immunized with the irrelevant IgMκ mAb or PBS did not demonstrate a rise in anti-LOS IgG, indicating specificity of the anti-CA1 Ab3 response (FIG. 2). In the figure, each point represents the mean of 2 experiments.

Figure 3:
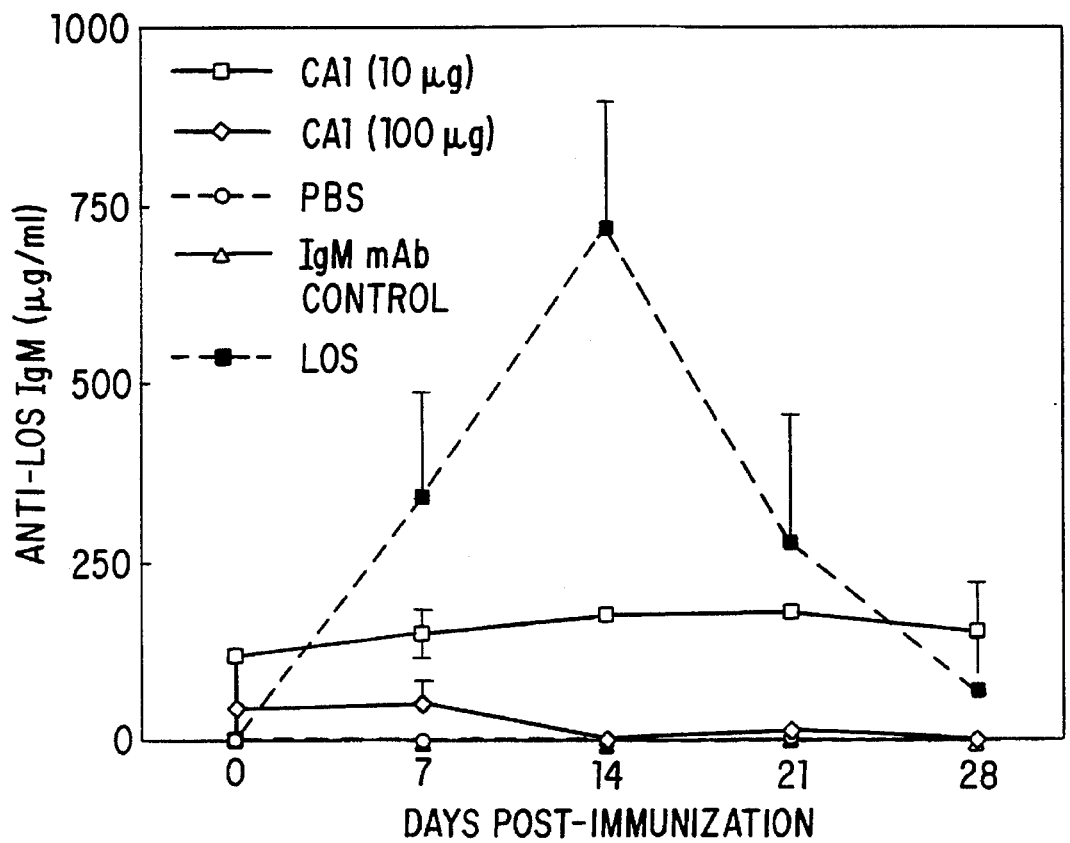
FIG. 3 depicts IgM anti-LOS antibody (Ab3) levels in syngeneic mice immunized with mAb CA1 (Ab2), control mAb, PBS and LOS.

IgM responses to immunization were also measured. There was no anti-LOS IgM response to CA1 in mice. As expected, a 4 fold IgM antibody response, which peaked 14 days post primary immunization and fell despite subsequent booster doses, developed in the mouse receiving LOS. Immunization with irrelevant IgMκ mAb or PBS elicited no IgM response (FIG. 3). In the figure, each point represents the mean of 2 experiments.

These results indicate that CA1 (Ab2) is capable of inducing anti-LOS Ab3 antibody. The rapid increase in IgG antibody production after boosting (FIG. 2) is suggestive of a T-cell dependent antibody response.

(b) Immunization of rabbits (xenogeneic)

To further confirm that the CA1 is a molecular mimic of the primary LOS epitope (ie., that CA1 represents an Ab2β), we performed immunizations in a xenogeneic system (rabbits). Six week old New Zealand white rabbits were immunized with CA1 and boosted (at 14 days) subcutaneously with varying doses (5, 10, 50 or 100) μg) of CA1, or control 100 μg of LOS, 100 μg of group C meningococcal capsular polysaccharide (C-MCP), 100 μg of irrelevant monoclonal murine IgMκ (all coupled to KLH in Complete Freund's Adjuvant [CFA] for subcutaneous immunization). For intravenous (iv) boosting, CA1 was given without KLH and CFA. The primary and booster immunizations consisted of the same dose of the original antigen. Rabbits were bled before the primary immunization and then weekly for 7 weeks. After this 7 week period, they were bled prior to each subsequent boost. Anti-LOS (Ab3) IgG and IgM antibody levels were determined by ELISA.

Figure 4:
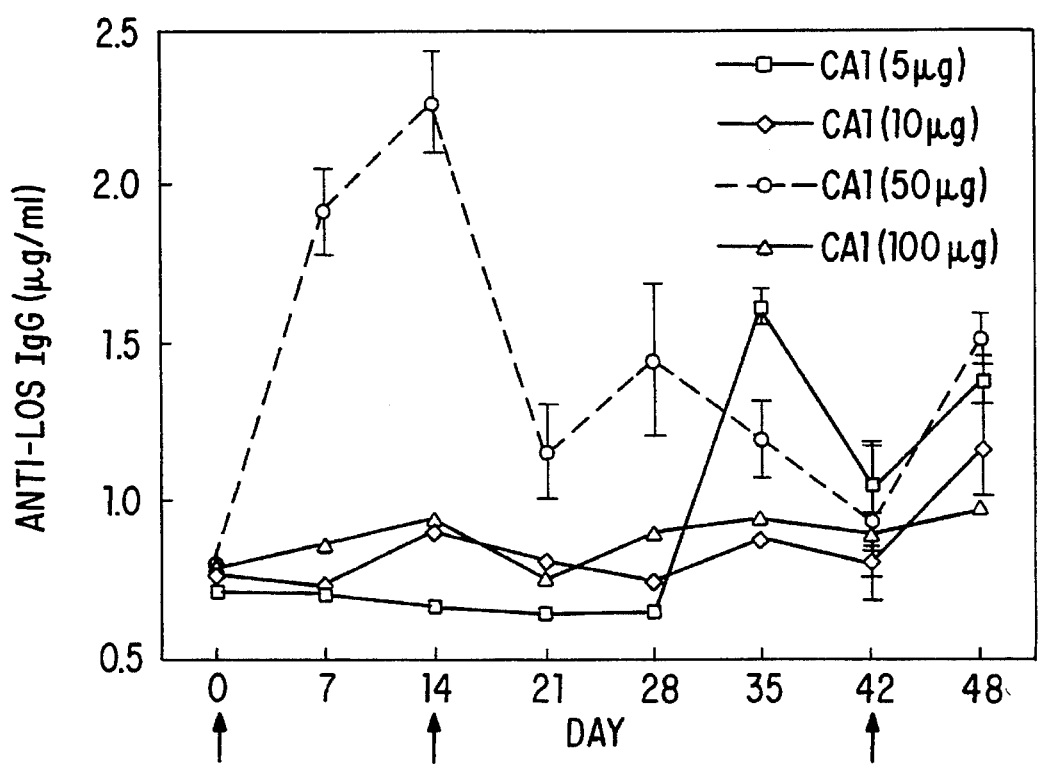
FIG. 4 depicts IgG anti-LOS antibody (Ab3) levels in xenogeneic rabbits immunized subcutaneously with varying doses of mAb CA1 conjugated to KLH. In the figure, the arrows indicate the initial and booster immunizations.

One animal was used for each of the doses. The rabbit immunized with 5 μg of CA1 developed a 2.25 fold rise in anti-LOS IgG antibody levels at 35 days and a 2 fold rise again on day 48 after a booster (FIG. 4). The rabbit immunized with 10 μg, had a slow initial rise to 1.5 fold over baseline on day 48. The rabbit immunized with 50 μg, developed a 2.8 fold rise on day 14 and stabilized at 2 fold over baseline after 48 days. The antibody level fell despite subsequent boosting until 32 weeks and the rabbit died at week 58 (data not shown). The death of this rabbit was unrelated to the subcutaneously administered mAb CA1 (Ab2), because the last dose had been given 26 weeks earlier. The rabbit immunized with 100 μg, did not develop an Ab3 IgG response (FIG. 4). In FIG. 4, each point represents the mean of 2 experiments.

Figure 5:
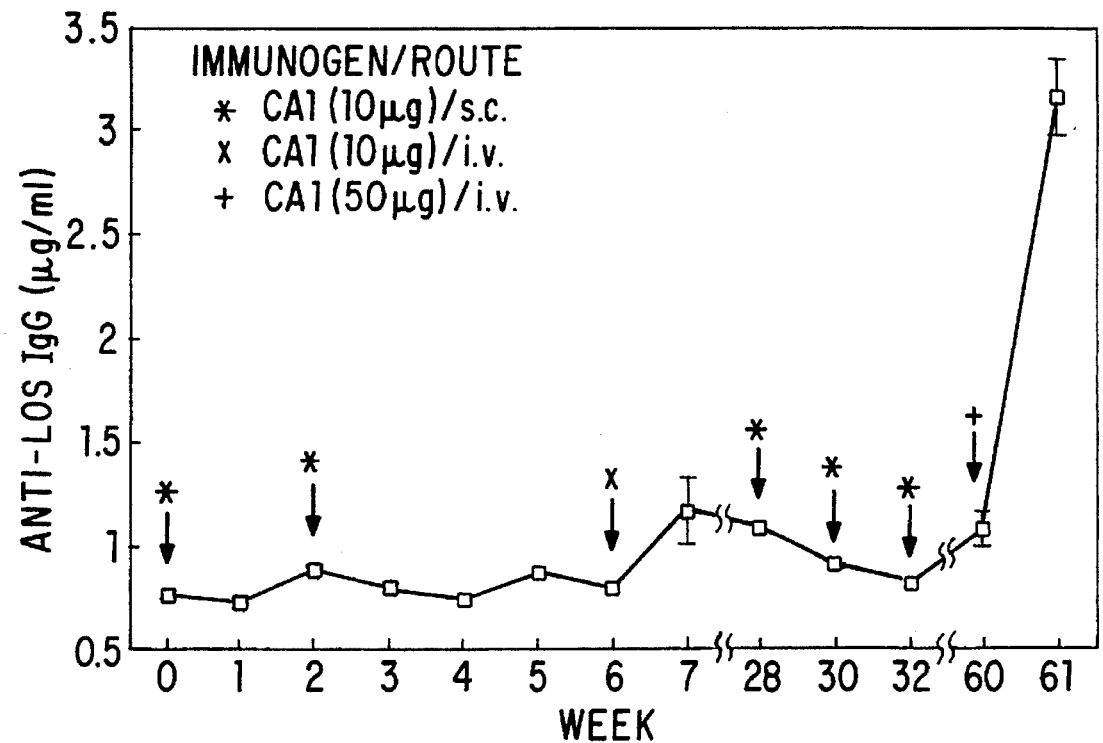
FIG. 5 depicts IgG anti-LOS levels in a xenogeneic rabbit given booster doses of mAb CA1. In the figure, the arrows indicate the initial and booster immunizations. The symbols indicate the route of initial and booster immunizations.

The rabbit that was initially immunized with 10 μg of CA1, was boosted iv with 50 μg of the same antigen (without KLH) on week 60 and developed a brisk 4 fold rise in antibody level 5 days after the boost (FIG. 5), suggestive of a T-cell dependent antibody response. In FIG. 5, each point represents the mean of 2 experiments.

Figure 6:
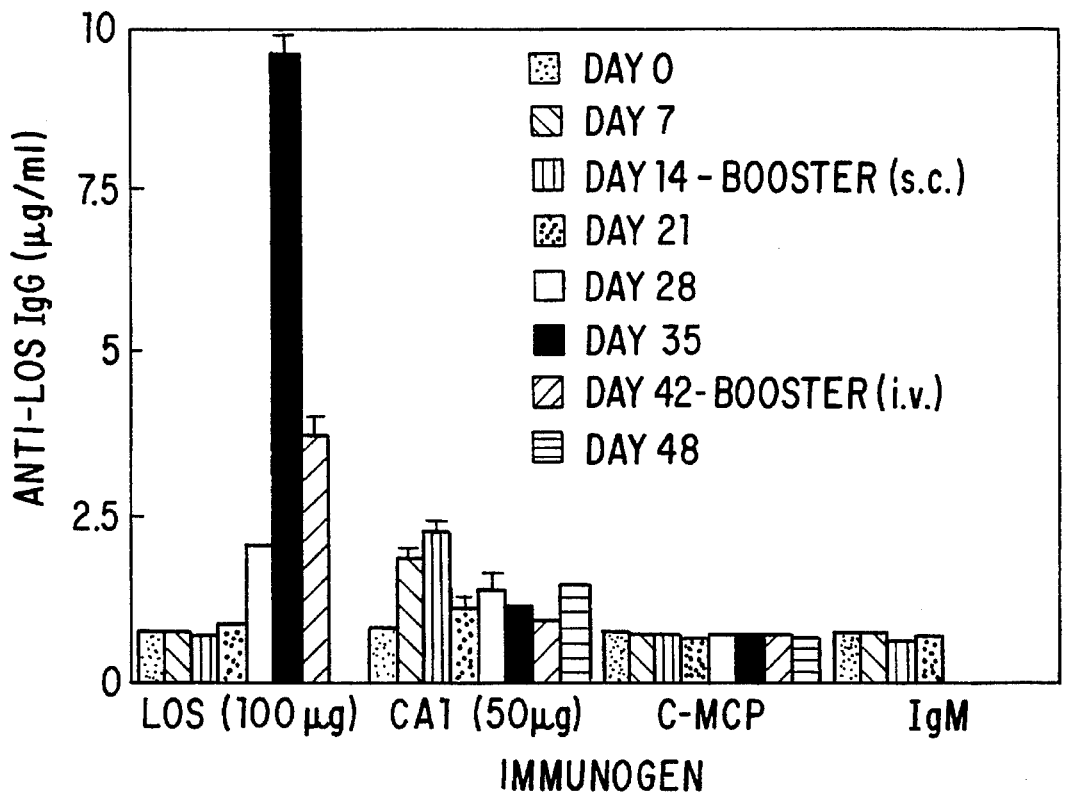
FIG. 6 depicts a comparison of IgG anti-LOS (Ab3) levels in xenogeneic rabbits immunized with mAb CA1, a control mAb, LOS and C-MCP.

One animal was used for each of the immunogens. In comparing the IgG Ab3 responses to CA1 (50 μg) with control immunogens LOS, C-MCP and irrelevant IgMκ, the anti-LOS response to 50 μg of CA1 (a 2.8 fold rise) was comparable to the response in the rabbit given LOS-KLH out to day 28 (2.6 fold rise) (FIG. 6). Thereafter, the rabbit immunized with LOS and boosted on day 14 developed an LOS antibody level 12 fold higher than the preimmunization level by 5 weeks. In FIG. 6, each point represents the mean of 2 experiments.

Figure 7A:
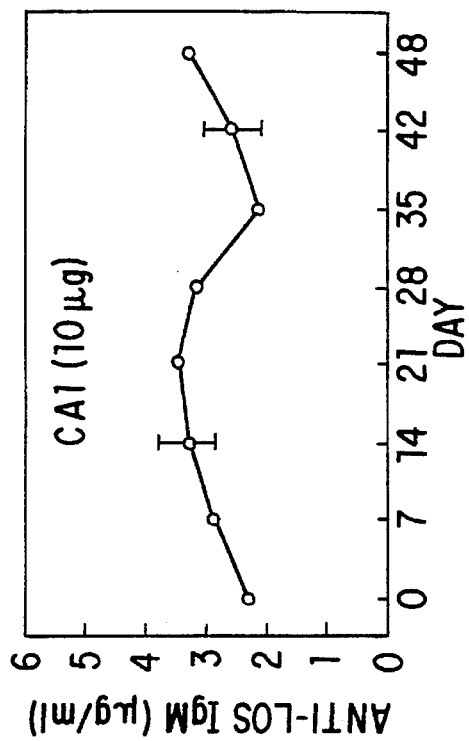
FIGS. 7A to 7F, together, depict the comparative anti-LOS IgM (Ab3) response in rabbits immunized with varying doses of CA1-KLH (FIGS. 7A–7D), C-MCP (FIG. 7E) and a control mAb (FIG. 7F).
Figure 7B:
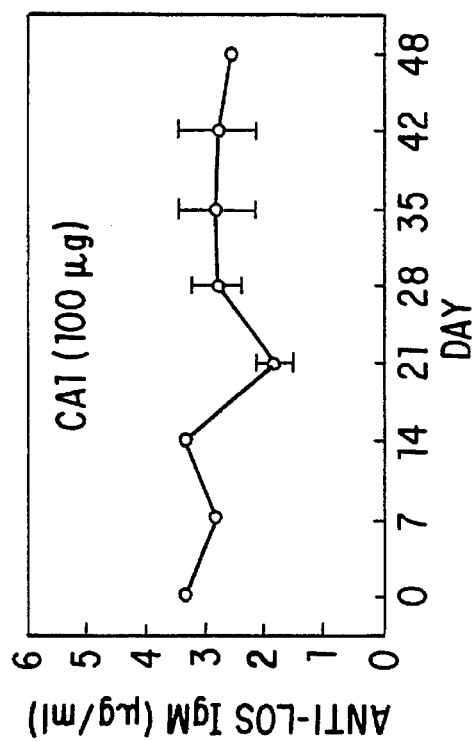
Figure 7C:
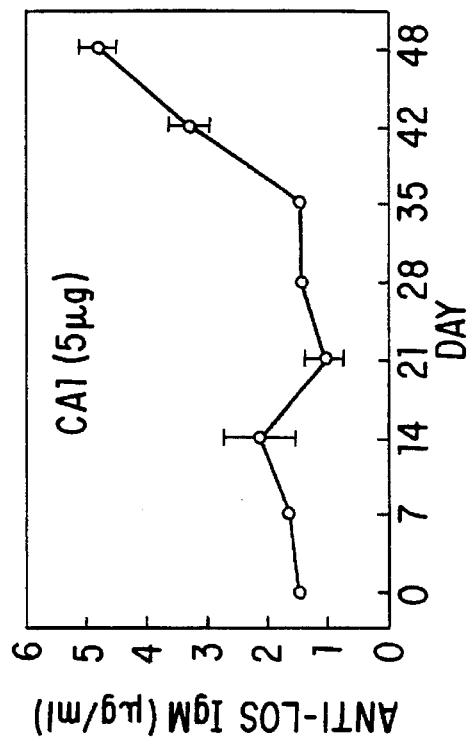
Figure 7D:
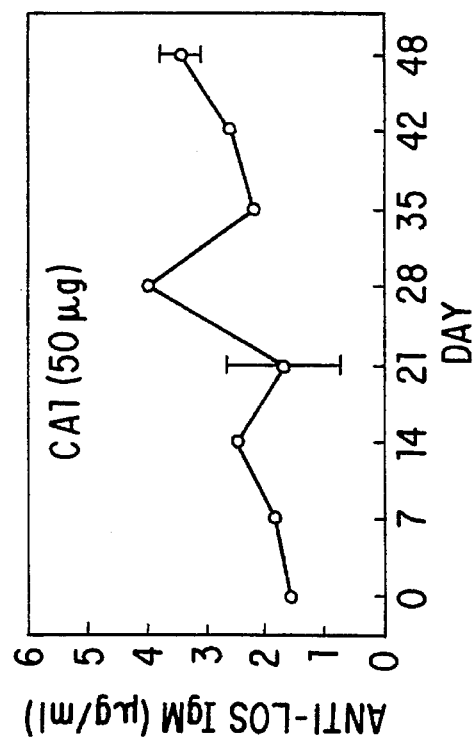
Figure 7F:
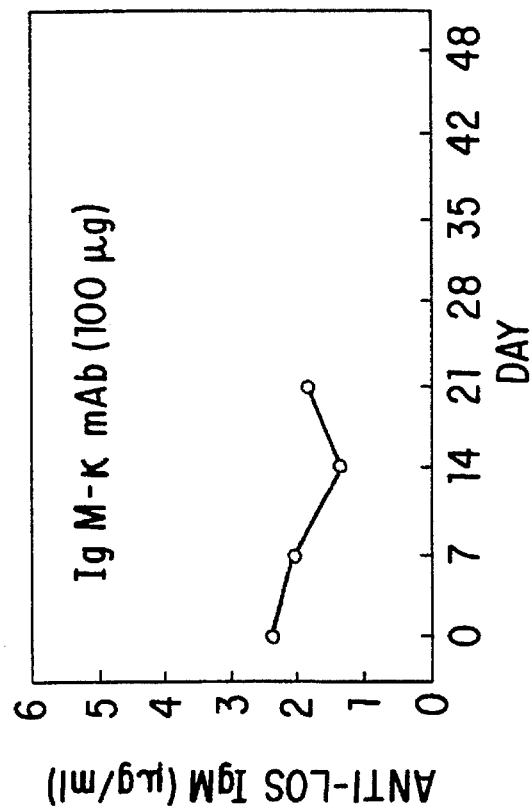
Figure 7E:
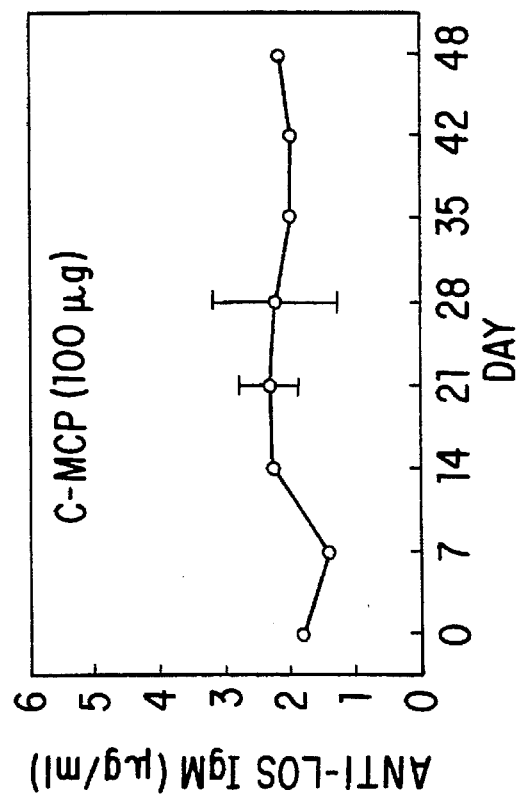

One animal was used for each of the immunogens. The maximum IgM Ab3 antibody response (a 3.3 fold rise) developed by day 48 in the rabbit that received the 5 μg dose of CA1 (FIG. 7A). The rabbit receiving 50 μg of CA1 developed a 2.5 fold rise by day 28 (FIG. 7C). Rabbits receiving a 10 or 100 μg dose did not develop an IgM Ab3 response (FIG. 7B and FIG. 7D). No response (either IgG or IgM antibody) was seen in the rabbits given C-MCP-KLH (FIG. 7E) and irrelevant IgM-KLH (FIG. 7F). In FIGS. 7A–7F, each point represents the mean of 2 experiments.

Figure 8:
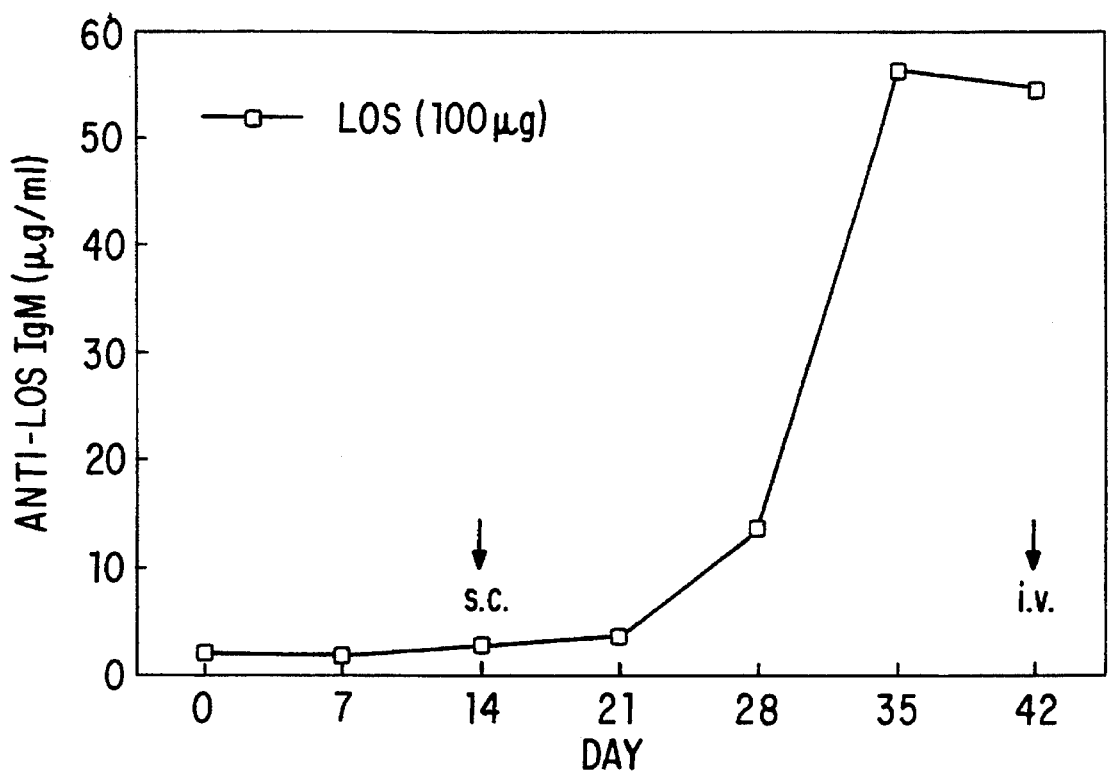
FIG. 8 depicts the IgM anti-LOS response in a rabbit immunized with 100 μg of LOS. In the figure, the arrows indicate the initial and booster immunizations.

The control rabbit immunized with LOS developed a 6.7 fold rise in IgM antibody level by day 28 and 27.5 fold rise by 5 weeks (FIG. 8). This rabbit died after an iv boost of 100 μg of LOS (without KLH) at 6 weeks. Subsequent antibody determinations in this animal showed that it had large quantities of circulating anti-LOS antibody (IgG and IgM). When the LOS was administered intravenously, an antigen-antibody reaction occurred causing a systemic Arthus reaction (or serum sickness), which activated complement and killed the animal. In FIG. 8, each point represents the mean of 2 experiments.

Taken together, these results confirm that the Ab3 response to CA1 is directed against the primary LOS antigen, indicating that the CA1 represents an Ab2β anti-idiotope mimic of the LOS epitope.

V. Functional activity of Ab1 and Ab3

(a) Bactericidal activity

Complement dependent bactericidal antibody activity of Ab1 (mAb 2C7) and Ab3 (response to CA1 and LOS in both mice and rabbits) was determined using established bactericidal assay procedures (15, 24, 41). Homologous complement sources were absorbed with glutaraldehyde-fixed gonococci representing SS (24-1) and a SR (WG) gonococci containing 2C7 epitope and a SR (71H) gonococci deficient in the epitope to remove antigonococcal antibodies prior to use of these complement sources in the assays.

Figure 9:
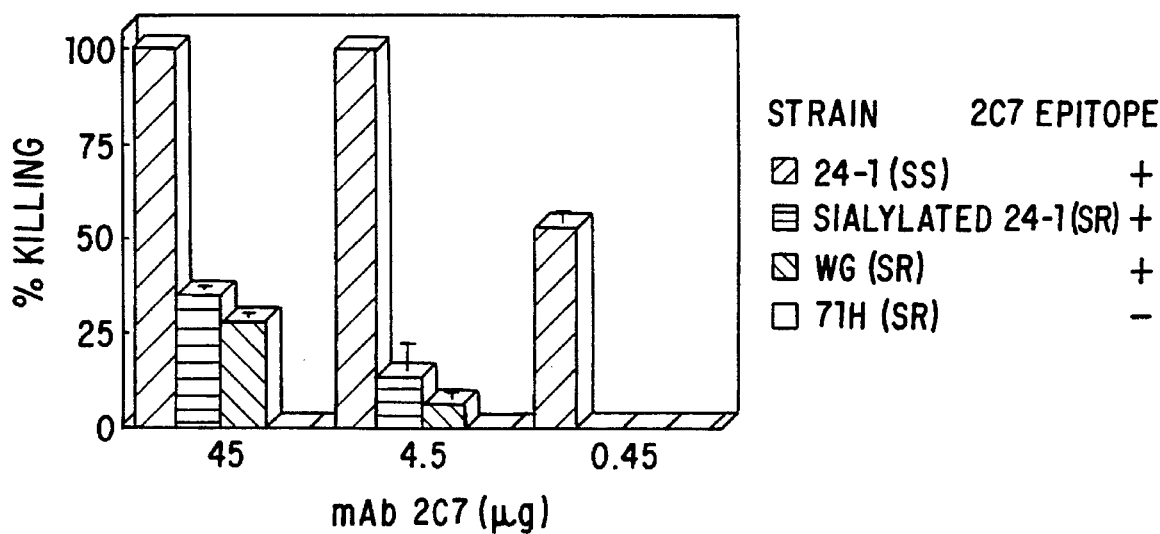
FIG. 9 depicts the bactericidal activity of mAb 2C7 against stable serum resistant (SR) bacterial strains WG, 71H and one serum sensitive (SS) strain 24-1, sialylated and non-sialylated.

Forty five μg of mAb 2C7 (Ab1) in the reaction mixture (the highest concentration used) mediated 100% killing of the SS gonococci 24-1, 36% killing of the sialylated (phenotypically SR) gonococci 24-1, and 29% killing of SR gonococci WG (all bearing the 2C7 epitope). Ab1 was unable to kill, at any concentration used, SR gonococci (71H) that lack the 2C7 LOS epitope (FIG. 9).

Figure 10:
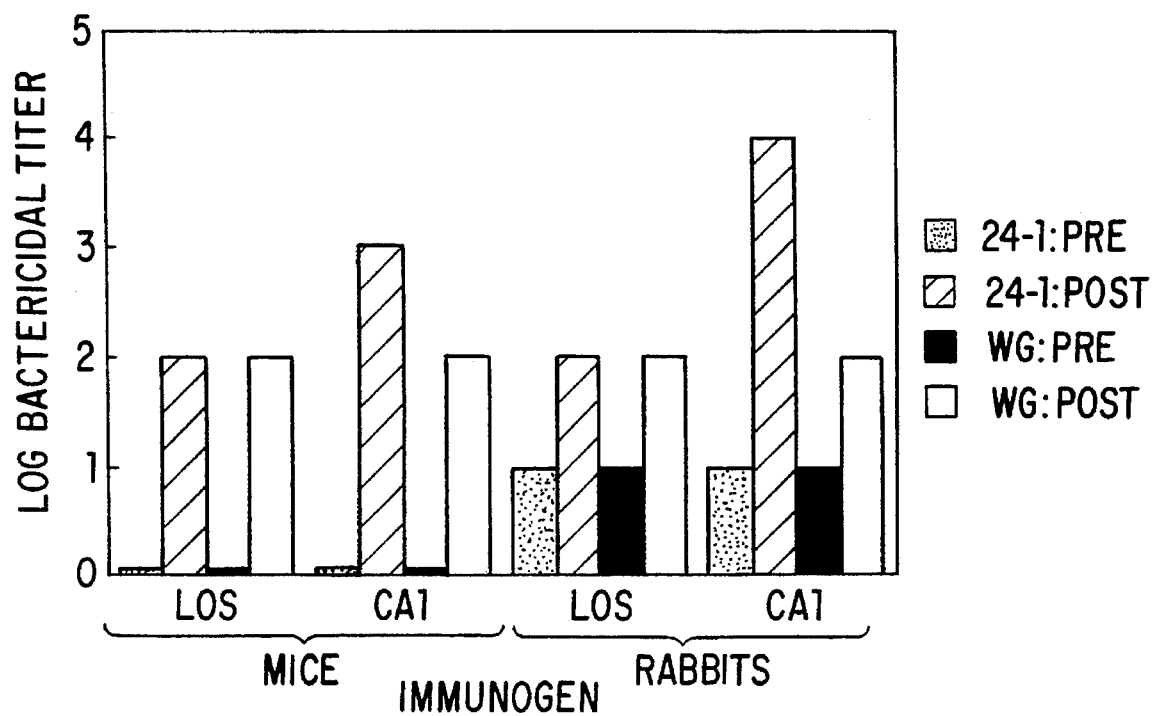
FIG. 10 depicts the bactericidal activity of post-CA1 and LOS immunization sera from mice and rabbits.

Ab3 antibodies induced by CA1 immunization possessed 10 fold greater killing activity against gonococcus 24-1 in both mice and rabbits than Ab3 antibodies induced by LOS immunization. CA1 immunization also elicited a bactericidal response against SR gonococcus WG in both mice and rabbits (FIG. 10), but not against gonococcus 71H (a control SR gonococcus which lacks the 2C7 epitope; data not shown).

Post-immunization sera from animals given control immunogens (an irrelevant murine mAb IgMk and N, meningitidis group C capsular polysaccharide [C-MCP]) did not contain bactericidal activity against any of the SS or SR gonococci.

(b) Opsonophagocytic activity (i) Staining of the organisms

Figure 11B:
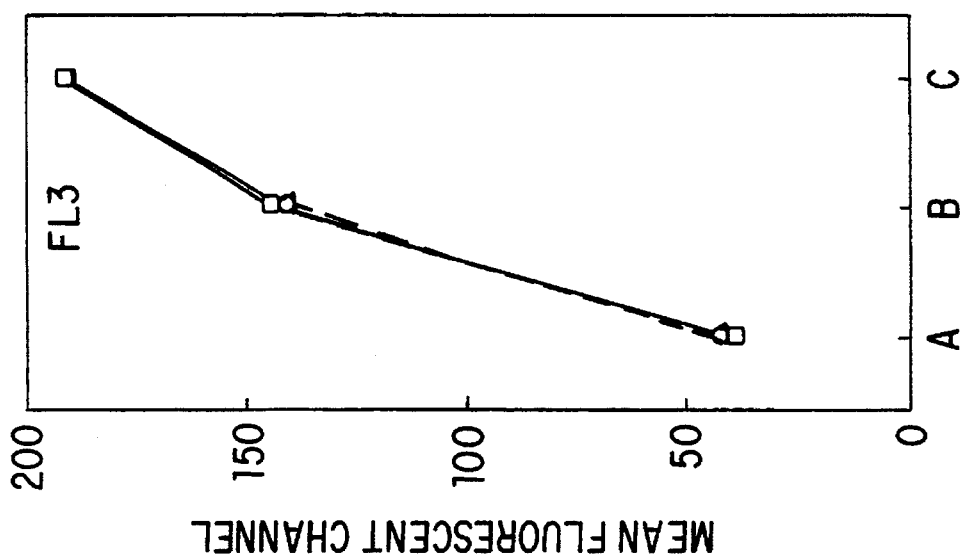
FIGS. 11A and 11B, together, depict the immunofluorescence levels of bacterial strains 24-1, WG and 71H, strained with Lucifer yellow alone (FIG. 11A) or with Lucifer yellow and streptavidin-PE-Texas red (FIG. 11B).
Figure 11A:
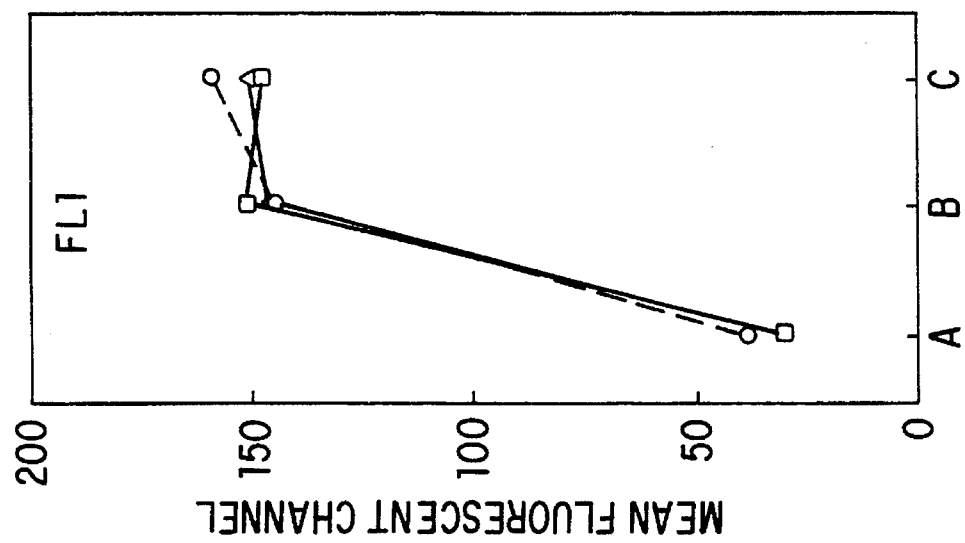

Unstained gonococci had low mean fluorescence (<40). After staining organisms homogeneously with lucifer yellow, the mean fluorescence increased about 5-fold in the FL1 channel and 3.5 fold in the FL3 channel. When organisms were counterstained with Strepavidin-Phycoerythrin (PE)-Texas red (SAPETR) via biotin labelled mAb 2C3, there was an additional 1.5-fold increase fluorescence in the FL3 channel, with no increase in the FL1 channel (FIG. 11). These results indicate that counterstaining of the organisms with SAPETR does not saturate the green fluorescence. In other words, lucifer yellow maintains its mean fluorescence in the FL1 channel despite counterstaining with SAPETR.

(ii) Effect of opsonizing antibody Ab1 (mAb 2C7)

Adherence of SS and SR gonococci to PMNs

Organisms present at time 0 are adherent to PMNs but are not yet ingested. Therefore, all organisms present were counterstained with SAPETR via biotinylated mAb 2C3. At time 0, the mean fluorescence expressed correlates directly with the intensity of the fluorescence (e.g., the higher the mean fluorescence of the PMNs, the greater the number of organisms adherent to the PMNs).

In the absence of opsonizing antibody, more SS gonococci (24-1) adhered to PMNs than do SR gonococci (34.91% more than WG and 38.10% more than 71H).

The effect of opsonization by mAb 2C7 (Ab1) upon adherence was determined for three strains. Mouse complement was added in experiments with SR and SS gonococci to examine the possibility that opsonophagocytosis is dependent on complement as well as antibody. C5 deficient complement was used for SS organisms to prevent the effects to membrane attack complex (C5b-9 or MAC) insertion while still permitting C3b and its derived fragments to act as opsonins. These complement sources were absorbed with glutaraldehyde-fixed gonococci to remove specific antibody prior to use in the assays. In control experiments, both complement sources were heated to 56° C. for 30 minutes prior to their use.

Figure 12:
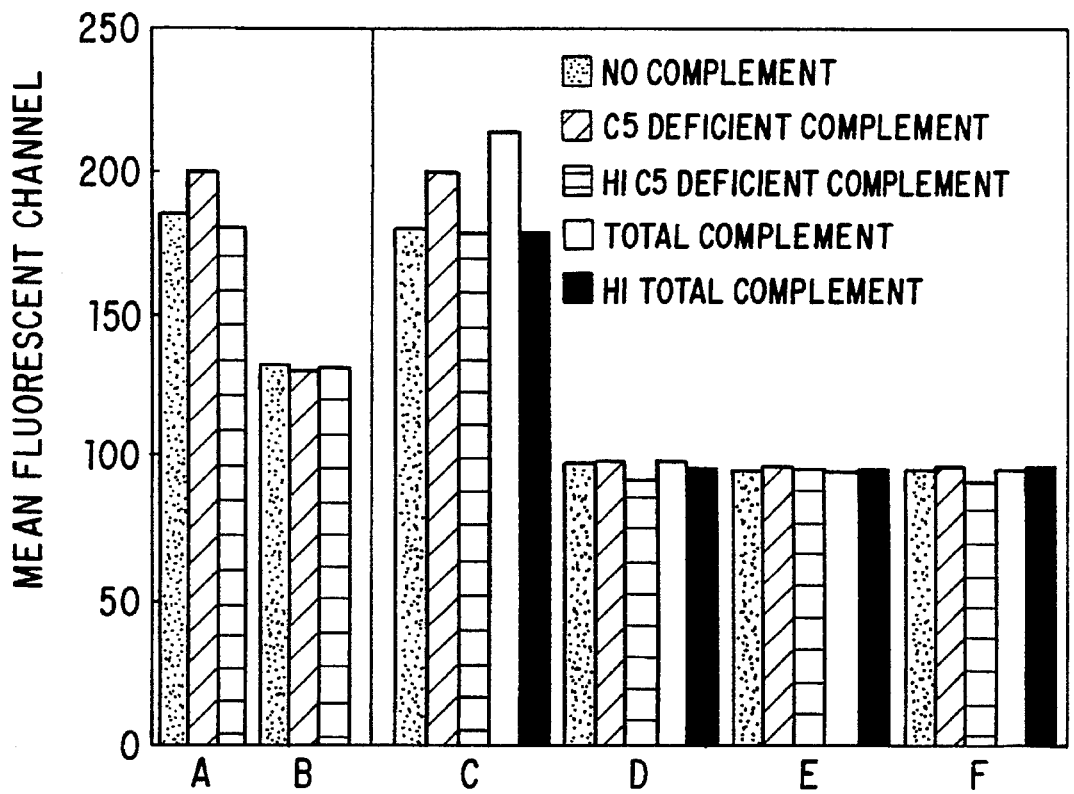
FIG. 12 depicts the effect of mAb 2C7 antibody on the adherence of bacteria to PMNs determined by quantitative immunofluorescence of lucifer yellow treated gonococci adherent to PMNs. In the figure, the results are indicated as follows.

The effect of mAb 2C7 (Ab1) antibody on adherence of organisms to PMNs is shown in FIG. 12. Opsonization of SS 24-1 gonococci with mAb 2C7 increased adherence 40.2% compared to adherence by non-opsonized organisms. Adherence of SR gonococci (WG) opsonized with mAb 2C7 to PMNs increased 83.9% compared to adherence by non-opsonized WG gonococci. Adherence to PMNs of SR gonococci (71H) lacking the 2C7 epitope was not effected by the addition of mAb 2C7.

Complement only minimally increased adherence of opsonized organisms bearing the 2C7 epitope to PMNs. Addition of C5-deficient complement resulted in an additional increase in mean fluorescence of 7.89% for SS gonococci (24-1) and 11.05% for SR gonococci (WG). However, addition of total complement to SR gonococci (WG) was 7.3% more effective than C5-deficient complement in facilitating adherence to PMNs.

These data suggest that: i) mAb 2C7 (Ab1) alone can enhance the adherence of organisms bearing the 2C7 epitope to PMNs and ii) the addition of complement further enhances adherence.

Phagocytosis of SS and SR gonococci by PMNs

PMNs with adherent organisms were incubated at 37° C. for 10, 20, and 30 minute periods. The mean fluorescence that resulted from Lucifer yellow remained constant throughout the incubation period, indicating that the total number of organisms remained constant and that ingestion of organisms did not effect emission of fluorescence. Decrease in red fluorescence indicated the internalization of organisms because these were not labelled with SAPETR via biotinylated 2C3 (FIGS. 13A–13F).

Nonopsonized SS gonococci (24-1) were initially ingested rapidly at 37° C. (10.17% in 10 minutes). No further ingestion occurred during the 30 minute incubation. Nonopsonized SR gonococci (WG and 71H) were not ingested during the first 20 minutes of incubation at 37° C. Between 20 and 30 minutes 16.30% of WG gonococci and 22.02% of 71H gonococci were ingested.

When opsonized with Ab1, SS gonococci 24-1 were ingested at a faster rate initially than SR gonococci WG (12.95% vs. 7.07% after 10 minutes at 37° C.). By 20 minutes, ingestion had equalized (28.64% vs. 32.34%). At 30 minutes, ingestion of 24-1 had increased to 37.57% with no further ingestion of WG.

After addition of 10% C5-deficient complement to the assay mixture, ingestion at 20 minutes of SS (24-1) and SR (WG) gonococci was comparable (43.53% vs. 40.01%). At 30 minutes, ingestion of SS gonococci was greater than SR gonococci (53.22% vs. 39.43%). However, when total complement was added to SR gonococci, ingestion at 30 minutes increased to 53.94%.

The difference in the rate of ingestion between opsonized and nonopsonized organisms was compared to determine the effect of Ab1 alone on ingestion. After 30 minutes incubation at 37° C., opsonization with Ab1 increased internalization of SS gonococci (24-1) by 26.92% and of SR gonococci (WG) by 16.21%. The addition of an active complement source further enhanced the internalization of the organisms. Neither opsonization with Ab1 nor addition of complement increased internalization of SR gonococci (71H) which lack the 2C7 epitope.

(iii) Effect of opsonizing antibody Ab3 (post-immune rabbit sera)

Adherence of SS and SR gonococci to PMNs

When opsonized with pre-immune rabbit serum, PMN adherence of SS gonococci (24-1) was greater than that of SR gonococci WG and 71H (51.67% and 23.59%, respectively, FIG. 14). When post-immune rabbit serum (Ab3) was used as an opsonin, SS gonococci (24-1) still exhibited greater adherence to PMNs than SR gonococci WG and 71H (17.48% and 27.91% greater, respectively). Comparing pre- and post-immune rabbit sera (Ab3), opsonization with Ab3 increased ingestion of SS gonococci (24-1) by 14.3% and of SR gonococci (WG) by 47.56%. There was no difference in adherence of SR gonococci (71H) lacking the 2C7 epitope regardless of the opsonin used.

Phagocytosis of SS and SR gonococci by human PMNs

Opsonized organisms adherent to PMNs were incubated at 37° C. for 10, 20 and 30 minutes (FIGS. 15A–15C). When pre-immune rabbit serum was used as the opsonin, SS gonococci (24-1) were only ingested minimally (9.13%). There was no ingestion of either SR gonococcal strain when opsonized with pre-immune rabbit serum.

When Ab3 (post-Ab2 immunization rabbit serum) was used as the opsonin, 34.98% of SS gonococci 24-1 and 35.25% of SR gonococci WG were ingested after 30 minutes at 37° C. Neither opsonin caused ingestion of SR gonococci lacking the 2C7 epitope (71H).

These data suggest that xenogeneic Ab3 elicited by Ab2 immunization is specific for the 2C7 OS epitope leading to enhanced binding and internalization of gonococci bearing the 2C7 epitope. Additionally, the rate of ingestion was comparable to or better than that seen when gonococci were opsonized with Ab1 (mAb 2C7). The increase in the rate of ingestion due to opsonization of SS gonococci (24-1)_ with Ab1 alone was 26.92% and that due to Ab3 was 34.98% (i.e., 1.3-fold greater ingestion). The increase in the rate of ingestion due to opsonization of SR gonococci (WG) with Ab1 alone was 16.21% and that due to Ab3 was 35.25% (a 2-fold increase). Taken together, these data indicate that the xenogeneic Ab3 response to Ab2 immunization is functionally specific for the 2C7 OS epitope. Thus, mAb CA1 (Ab2) represents an Ab2$\beta$ that mimics the nominal gonococcal OS epitope.

A hybridoma producing anti-idiotypic antibodies according to the present invention is exemplified by a culture deposited in the American Type Culture Collection (12301 Parklawn Drive, Rockville, Md. 20852 U.S.A) (ATCC) on Mar. 26, 1993 and was assigned ATCC accession number HB 11311.

Hybridoma 2C7 secreting the mAb 2C7 of this invention exemplified by a cell culture designated as 2C7 and deposited the ATCC on Mar. 9, 1995. This culture was assigned ATCC accession number HB-11859.

While we have hereinbefore described a number of embodiments of this invention, it is apparent that our basic constructions can be altered to provide other embodiments which utilize the processes and compositions of this invention. Therefore, it will be appreciated that the scope of this invention is to be defined by the claims appended hereto rather than by the specific embodiments which have been presented hereinbefore by way of example.

LITERATURE CITED

1. Apicella, M. A., M. A. J. Westerink, S. A. Morse, H. Schneider, P. A. Rice and J. M. Griffiss. 1986. Bactericidal antibody response of normal human serum to the lipooligosaccharide Neisseria gonorrhoeae. J. Infect. Dis. 153: 520–526.

2. Apicella, M. A., R. E. Mandrell, M. Shero. 1990. Modification of sialic acid of Neisseria gonorrhoeae lipooligosaccharide epitope expression in human urethral exudates: an immunoelectron microscopic analysis. J. Infect. Dis. 162: 506–512.

3. Blake, M. S., K. H. Johnston, G. J. Russel-Jones and E. C. Gotschlich. 1984. A rapid, sensitive method for detection of alkaline phosphatase-conjugated antiantibody on western blots. Anal. Biochem. 136: 175–179.

4. Britigan, B. E., M. S. Cohen and P. F. Sparling. 1985. Gonococcal infection: a model of molecular pathogenesis. N. Eng. J. Med. 312: 1683–1694.

5. Brooks, G. F. and C. J. Lammel. 1989. Humoral immune response to gonococcal infection. Chn. Micro. Rev. 2S: S5-S 10.

6. CDC/NIH Workshop on pelvic inflammatory disease: Prevention, Management and Research Directions in the 1990's. September 1990.

7. CDC. 1982. Sexually transmitted diseases treatment guidelines. MMWR. 31: Suppl 2: S37–S42.

8. CDC. 1984. Chromosomally mediated resistant Neisseria gonorrhoeae-United States. MMWR. 33: 408–410.

9. CDC. 1990. Summary cases of specified notifiable diseases United States. MMWR. 38: 891.

10. Chase, M. W. 1968. Appendix 11, Buffers. In: Methods in Immunology and Immunochemistry. C. A. Williams and M. W. Chase. (ed.). Academic Press, Inc, New York. p. 389–395.

11. Cohen, I. R., D. S. Kellogg and L. C. Norins. 1969. Serum antibody response in experimental human gonorrhoeae: immunoglobulins G, A and M. Br. J. Ven. Dis. 45: 325–327.

12. Densen, P., S. Gulati and P. A. Rice. 1987. Specificity of antibodies against Neisseria gonorrhoeae that stimulate neutrophil chemotaxis. J. Clin. Invest. 80: 78–87.

13. Dunn, P. A. and H. W. Tyrer. 1981. Quantitation of neutrophil phagocytosis using fluorescent latex beads. Correlation of microscopy and flow cytometry. J. Lab. Clin. Med. 98: 374–381.

14. Engvall, E. and P. Perlman. 1972. Enzyme-linked immunosorbent assay, ELISA. J. Immunol. 102: 129–135.

15. Fohn, M. J., T. A. Mietzner, T. W. Hubbard, S. A. Morse and E. W. Hook. 1987. Human immunoglobulin G antibody response to the major gonococcal iron-regulated protein. Infect. Immun. 55: 3065–3069.

16. Gebhard, D. F. Jr., A. Mittelman, A. Cirrincione, H. T. Thaler and B. Koziner. 1986. Comparative analysis of surface membrane immunoglobulin determination by flow cytometry and fluorescence microscopy. J. Histochem. & Cytochem. 34: 475–481.

17. Glynn, A. A. and M. E. Ward. 1970. Nature and heterogeneity of the antigens of Neisseria gonorrhoeae involved in the bactericidal reaction. Infect. Immun. 2: 162–168.

18. Gnehm, H. E., S. I. Pelton, S. Gulati and P. A. Rice. 1985. Characterization of antigens from nontypable Haemophilus influenzas recognization by human bactericidal antibodies. J. Chn. Invest. 75: 1645–1658.

19. Green, N. M. 1965. A spectrophotometric assay for avidin and biotin based on binding of dyes by avidin. Biochem. J. 94: 23C–24C.

20. Griffiss, H. M., J. P. O'Brien, R. Yamasaki, G. D. Williams, P. A. Rice and H. Schneider. 1987. Physical heterogeneity of Neisserial lipooligosaccharides reflects oligosaccharides that differ in apparent molecular weight, chemical composition, and antigenic expression. Infect. Immun. 55: 1792–1800.

21. Hawkes, R., E. Niday and J. Gorden. 1982. A dot immunobinding assay for monoclonal and other antibodies. Anal. Biochem. 119: 142–147.

22. Hnatowich, D. J., F. Virzi and M. Ruschowski. 1987. Investigations of avidin and biotin for imaging applications. J. Nucl. Med. 28: 1294–1302.

23. Insel, R. and P. Anderson. 1986. Haemophilus influenzas type b: Assays for the capsular polysaccharide and for polysaccharide antibody. p. 383. In: N. R. Rose, H. Friedman, J. L. Fahey. (ed.). Manual of clinical laboratory immunology. Washington, DC. ASM.

24. Jeme, N. K. 1974. Towards a network theory of the immune system. Ann. Inst. Pasteur. Immun. 125C: 373–389.

25. Joiner, K. A., R. Scales, J. A. Warren, M. M. Frank and P. A. Rice. 1985. Mechanism of action of blocking immunoglobulin G for Neisseria gonorrhoeae. Clin. Invest. 76: 1765–1772.

26. Jones, P. T., P. H. Dear, J. Foote, M. S. Neuberger and G. Winter. 1986. Replacing the Complementarity-Determining Regions in a Human Antibody with Those From a Mouse. Nature 321: 522–525.

27. Kasper, D. L., P. A. Rice and W. M. McCormack. 1977. Bactericidal antibody in genital infection due to Neisseiia gonorrhoeae. J. Infect. Dis. 135:243–251.

28. Kennedy, R. C. and K. Adler-Storthe. 1983. Immune response to hepatitis B surface antigen: enhancement by prior injection of antibodies to the idiotype. Science 221: 853–854.

29. Kennedy, R. C., J. E. Eichberg, R. E. Landford and G. R. Dressman. 1986. Anti-idiotypic vaccine for type B viral hepatitis in chimpanzees. Science. 232: 220–223.

30. Kieber-Emmons, T., R. E. Ward, S. Raychaudhuri, R. Rein and H. Kohler. 1986. Rational design and application of idiotype vaccines. Int. Rev. Immunol. 1: 1–26.

31. Kohler, G. and C. Milstein. 1975. Continuous Cultures of Fused Cells Secreting Antibody of Predefined Specificity. Nature 256: 495–7.

32. Laemmli, U. K. 1970. Cleavage of structural proteins during the assembly of the head of bacteriophage T4. Nature 227: 680–685.

33. Lambden, P. R., J. E. Heckels, H. McBride and P. J. Watt. 1981. The identification and isolation of noval pilus types produced by variants of Neisseria gonorrhoeae P9 following selection in vivo. FEMS. Microbiol. Lett. 10: 339–341.

34. Lammel, C. J., R. L. Sweet, P. A. Rice, J. S. Knapp, G. K. Schoolnik, D. C. Heilbron and G. F. Brooks. 1985. Antibody-antigen specificity in the immune response to infection with Neisseria gonorrhoeae. J. Infect. Dis. 152: 990–1001.

35. Lerner, R. A. 1981. How to Make a Hybridoma. Yale J. Biol. Med., 54: 387–402.

36. Mandrell, R. E., H. Schneider, M. A. Apicelia, W. D. Zollinger, P. A. Rice and J. M. Griffiss. 1986. Antigenic and physical diversity of Neisseria gonorrhoeae lipooligosaccharides. Infect. Immun. 54: 63–69.

37. Mandrell, R. E., J. M. Griffiss and B. E. Macher. 1988. Lipooigosaccharides (LOS) of Neisseria gonorrhoeae and Neisseria meningitidis have components that are immunochemically similar to precursors of human blood group antigens: carbohydrate sequence specificity of the mouse monoclonal antibodies that recognize crossreacting antigens on LOS and human erythrocytes. J. Exp. Med. 168: 107–126.

38. Mishell, B. B. and S. Shiigi. 1980. Selected methods in cellular immunology. P. 303. W. H. Freeman & Co, New York.

39. Morse, S. A., S. Stein and J. Hines. 1974. Glucose metabolism in Neisseria gonorrhoeae. J. Bact. 120: 702-714.

40. McNamara, M. K., R. E. Ward, and J. Kohler. 1984. Monoclonal idiotope vaccine against Streptococcus pneumonia. A precursor study. J. Immunol. 139: 2775–2780.

41. Newhall, W. J., W. D. Sawyer, and R. A. Haak. Cross-linking analysis of the outer membrane protein of Neisseria gonorrhoeae. Infect. Innum. 28: 785–741.

42. Nisonoff, A. and E. Lamoyi. 1981. Implications of the presence of an internal image of the antigen in anti-idiotypic antibodies: possible application to vaccine production. Clin. Immunol. Immunopathol. 21: 397–406.

43. Rice, P. A. and D. L. Kasper. 1977. Characterization of gonococcal antigens responsible for gonococcal bactericidal antibody in disseminated infection. J. Clin. Invest. 60: 1149–1158.

44. Rice, P. A. and D. L. Kasper. 1982. Characterization of serum resistance of Neisseria gonorrhoeae that disseminate. J. Clin. Invest. 70: 157–167.

45. Rice, P. A., H. E. Vayo, M. R. Tam and M. S. Blake. 1986. Immunoglobulin G antibodies directed against protein III block killing of serum resistant Neisseria gonorrhoeae by immune serum. J. Exp. Med. 164: 1735–1748.

46. Rice, P. A. 1989. Molecular basis for serum resistance in Neisseria gonorrhoeae. Clin.Micro. Rev.2S: S112–SI17.

47. Roberts, R. B. 1967. The interaction in vitro between Group B meningococci and rabbit polymorphonuclear leukocytes. J. Exp. Med. 126: 795–819.

48. Ross, S. C. and P. Densen. 1985. Opsonophagocytosis of Neisseria gonorrhoeae: interaction of local and disseminated isolates with complement and neutrophils. J. Infect. Dis. 151: 33–41.

49. Schoolnik, G. K. and Mietzner, T. A. 1992. Vaccines against gonococcal infections. p. 565–597. In: G. C. Woodrow and M. M. Levine (ed.). New Generation Vaccines. Marcel Dekker, Inc. New York.

50. Schoolnik, G. K. and Z. A. McGee. 1985. Gonococcal vaccine development strategies: summary of the recommendations of a National Institutes of Health vaccine panel. p. 329–331. In: G. K. Schoolnik, G. F. Brooks, S. Falkow, C. E. Frasch, J. S. Knapp, J. A. McCutchan and S. A. Morse. (ed.). The pathogenic neisseria. ASM. Washington D.C.

51. Schreiber, J. R., M. Patarawan, M. Tosi, J. Lennon and G. B. Pier. 1990. Anti-idiotype-induced lipo-oligosaccharide specific response to Pseudomanas aeroginosa. J. Immun. 144: 1023–1029.

52. Schreiber, J. R., G. B. Pier, M. Grout, K. Nixon and M. Patawaran. 1991. Induction of opsonic antibodies to Pseudomonas aeroginosa mucoid exopolysaccharide by an anti-idiotypic monoclonal antibody. J. Infect. Dis. 164: 507–514.

53. Stein, K. E. and T. Soderstrom. 1984. Neonatal administration of idiotype or anti-idiotype primes for protection against Escherichia coli K13 infection in mice. J.Exp.Med. 160: 1001–1011.

54. Steinkamp, J. A., J. S. Wilson, G. C. Saunders and C. C. Stewart. 1982. Phagocytosis: Flow cytometric quantitation with fluorescent microspheres. Science. 215: 64–66.

55. Sveum, R. J., T. M. Chused, M. M. Frank and E. J. Brown. 1986. A quantitative fluorescent method for measurement of bacterial adherence and phagocytosis. J. Immun. 90: 257–264.

56. Swanson, J. 1979. Studies on gonococcus infection XVIII. I.[125] labelled peptide mapping of the major protein of the gonococcal cell wall outer membrane. Infect. Immun. 23: 799-781.

57. Swanson, J. 1982. Colony opacity and protein II composition of gonococci. Infect. Immun. 37: 359–368.

58. Tramont, E. C., J. C. Sadoff and M. S. Artenstein. 1974. Cross reactivity of Neisseria gonorrhoeae and Neisseria meningitidis and the nature of antigens involved in the bactericidal reactions. J. Infect. Dis. 130: 240–247.

59. Tramont, E. C. and J. Ciak. 1978. Antigonococcal antibodies in genital secretions. p. 274–278. In: G. F. Brooks, E. C. Gotschlich, W. D. Sawyer and F. E. Young (ed.). lmmunobiology of Neisseria gonorrhoeae. Washington D.C. ASM.

60. Tramont, E. C., J. W. Boslego, R. Chung, D. McChesney, J. Ciak, J. Sadoff, M. Piziak, C. C. Brinton, S. Wood and J. Bryan. 1985. Parenteral gonococcal pilus vaccine. p. 316–322. In: G. K. Schoolnik, G. F. Brooks, S. Falkow, C. E. Frasch, J. S. Knapp, J. A. McCutchan and S. A. Morse. (eds.). The pathogenic neisseria. Washington D.C. ASM.

61. Tramont, E. C. 1989. Gonococcal vaccines. Clin. Micro. Rev. 2S: S74–S77.

52. Ward, E. S., D. Güssow, A. D. Griffiths, P. T. Jones and G. Winter. Binding activities of a repertoire of a single immunoglobulin variable domains secreted from Escherichia coli. Nature 341: 544– 546.

63. Ward, M. E., P. J. Watt and J. N. Robertson. 1974. The human fallopian tube: a laboratory model for gonococcal infection. J. Infect. Dis. 129: 650– 659.

64. Ward, M. E., P. R. Lambden, J. E. Heckels and P. J. Ward. 1978. The surface properties of Neisseria gonorrhoeae: determinant of susceptibility to antibody complement killing. J. Gen. Micro. 108: 205–212.

65. Washington, A. E. 1982. Update on treatment recommendations for gonococcal infections. Rev. Infect. Dis. 4S: S758–S771.

66. Westerink, M. A. J., A. A. Campagnari, M. A. Wirth and M. A. Apicella. 1988. Development and characterization of an anti-idiotype antibody to the capsular polysaccharide of Neisseria meningitidis serogroup C. Infect. Immun. 56: 1120– 1127.

67. Westphal, O., O. Ludefitz and F. Bister. 1952. Uder die extraktion of bakterien mit phenol/wasser. Z. Naturforsch B7: 148–155.

68. U.S. Pat. No. 4,816,397, Boss et al. Mar. 28, 1989. Multichain Polypeptides Or Proteins And Processes For Their Production.

69. Brodin, N. T., J. Dahmén, B. Nilsson, L. Messeter, S. Mårtenson, J. Heldrup, H. O. Sjögren and A. Lundblad. 1988. Monoclonal antibodies produced by immunization with neoglycoproteins containing Galα→4β1→4Glcβ—O and Galα1→4β1→GlcNAcβ—O residues: useful immunochemical and cytochemical reagents for blood group P antigens and a differentiation marker in Burkitt lymphoma and other B-cell malignancies. Int. J. Cancer. 42:185–194.

70. Kim, J. J., R. E. Mandrell, H. Zhen, M. A. J. Westerink, J. T. Poolman and J. M. Griffiss. 1988. Electromorphic characterization and description of conserved epitopes of the lipooligosaccharides of group A Neisseria meningitidis. Infect. Immun. 56:2631–2638.

71. Mandrell, R. E. 1992. Further antigenic similarities of Neisseria gonorrhoeae lipooligosaccharides and human glycosphingolipids. Infect. Immun. 60:3017–3020.

We claim:

1. An anti-idiotypic monoclonal antibody, or binding fragment thereof, characterized by an antigen combining site which immunospecifically binds to the idiotype of a second antibody which binds to an oligosaccharide epitope of N. gonorrhoeae, which oligosaccharide epitope is not present in human blood group antigens, wherein the oligosaccharide epitope specifically binds to monoclonal antibody 2C7 produced by hybridoma HB-11859.

2. The anti-idiotypic monoclonal antibody, or binding fragment thereof, according to claim 1, wherein the second antibody binds to an oligosaccharide epitope which specifically binds to a monoclonal antibody produced by immunizing a mammal with an anti-idiotypic monoclonal antibody, or binding fragment thereof, produced by a hybridoma cell lane having the characteristics of HB 11311 as deposited with the ATCC.

3. An anti-idiotypic monoclonal antibody, or binding fragment thereof, produced by a hybridoma cell line having the characteristics of HB 11311 as deposited with the ATCC.

4. A hybridoma cell line that produces an anti-idiotypic monoclonal antibody, or a binding fragment thereof, according to any one of claims 1, 2 or 3.

5. The hybridoma cell line according to claim 4, which is HB 11311 as deposited with the ATCC.

6. A composition for diagnosis of N. gonorrhoeae infection comprising a diagnostically effective amount of an anti-idiotypic monoclonal antibody, or binding fragment thereof, according to any one of claims 1, 2, or 3.

* * * * *